(12) United States Patent
Petitte et al.

(10) Patent No.: US 7,994,388 B2
(45) Date of Patent: Aug. 9, 2011

(54) DEPLETION OF ENDOGENOUS PRIMORDIAL GERM CELLS IN AVIAN SPECIES

(75) Inventors: James N. Petitte, Raleigh, NC (US); Samuel Lloyd Pardue, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/541,947

(22) PCT Filed: Jan. 16, 2004

(86) PCT No.: PCT/US2004/001568
§ 371 (c)(1),
(2), (4) Date: Dec. 12, 2005

(87) PCT Pub. No.: WO2004/065558
PCT Pub. Date: Aug. 5, 2004

(65) Prior Publication Data
US 2006/0095980 A1 May 4, 2006

Related U.S. Application Data

(60) Provisional application No. 60/440,424, filed on Jan. 16, 2003.

(51) Int. Cl.
*A01K 67/027* (2006.01)
(52) U.S. Cl. .......................................... 800/19; 800/21
(58) Field of Classification Search .................... 800/21, 800/19
See application file for complete search history.

(56) References Cited

U.S. PATENT DOCUMENTS

| | | | |
|---|---|---|---|
| 4,357,272 | A | 11/1982 | Polson |
| 5,340,740 | A | 8/1994 | Petitte et al. |
| 5,656,479 | A | 8/1997 | Petitte et al. |
| 5,830,510 | A | 11/1998 | Petitte et al. |
| 6,156,569 | A | 12/2000 | Pounce de Leon et al. |
| 6,333,192 | B1 | 12/2001 | Petitte et al. |
| 6,354,242 | B1 | 3/2002 | Pardue et al. |
| 6,691,638 | B2 | 2/2004 | Pardue et al. |

(Continued)

FOREIGN PATENT DOCUMENTS

WO  WO 98/38283  9/1998

(Continued)

OTHER PUBLICATIONS

NCBI Sequence Listing for AAO26019, Jan 5, 2003.*

(Continued)

*Primary Examiner* — Michael C. Wilson
(74) *Attorney, Agent, or Firm* — Jenkins, Wilson, Taylor & Hunt, P.A.

(57) ABSTRACT

Methods for modulating primordial germ cell (PGC) numbers and/or development in avians are provided. In one embodiment, the presently disclosed subject matter provides a method for modulating primordial germ cells numbers in an avian embryo comprising immunizing a female bird with an antigen associated with primordial germ cells, whereby an egg produced by the female bird comprises a sufficiently high concentration of antibodies specific for the antigen to modulate numbers of endogenous PGCs in an avian embryo present within in the egg. Also provided are methods for producing chimeric avians, methods for increasing the proportion of male birds in a plurality of eggs, methods of producing avian gametes, and methods for enhancing germ line transmission of nucleic acids in birds.

17 Claims, 4 Drawing Sheets

U.S. PATENT DOCUMENTS

| | | | |
|---|---|---|---|
| 7,422,897 | B2 | 9/2008 | Petitte et al. |
| 2002/0162134 | A1 | 10/2002 | Baguisi et al. ............... 800/19 |
| 2003/0111016 | A1 | 6/2003 | Pardue |

FOREIGN PATENT DOCUMENTS

| | | |
|---|---|---|
| WO | WO 99/25863 | 5/1999 |
| WO | WO2004/065558 | 8/2004 |

OTHER PUBLICATIONS

Vick et al., "Transgenic Birds From Transformed Primordial Germ Cells", Proc. R. Soc. Lond. B.; 251; pp. 179-182, (1993).

Bresler et al., "Manipulations of Germ-Cell Populations in the Gonad of the Fowl", British Poultry Science, 35; pp. 241-247, (1994).

International Search Report and Notification of Transmittal with Written Opinion for PCT/US04/01568.

International Preliminary Report on Patentability, corresponding to PCT application No. PCT/US04/01568 dated Apr. 27, 2006.

Office Communication corresponding to a Chinese Patent Application Serial No. 200480007059.8 dated Jan. 15, 2007 (English translation included).

Office Communication corresponding to an EP Application Serial No. 04703077.0-2405 dated Feb. 15, 2007.

Tsukada et al., "Isolation and characterization of a cDNA clone encoding the germ cell-specific RNA binding protein dazl (deleted in azoospermia-like) from the chicken ovary," Unpublished, Submitted (Jan. 5, 2003) Animal Physiology, Graduate School of Bioagricultural Sciences, Nagoya University, Furo-cho, Chikusa-ku, agoya 464-8601, Japan.

Pain et al., "Chicken Embryonic Stem Cells and Transgenic Strategies," Cells Tissues Organs, vol. 165, pp. 212-219 (1999).

Chang et al., "Production of Germline Chimeric Chickens by Transfer of Cultured Primordial Germ Cells," Cell Biology International, vol. 21, No. 8, pp. 495-499 (1997).

Ponce de Leon et al, Rev. Bras. Reprod. Anim., vol. 21, No. 3, pp. 97-101 (1997).

Ono, "Transfer of Male or Female Primordial Germ Cells of Quail into Chick Embryonic Gonads," Exp. Anim., vol. 45(4), pp. 347-352 (1996).

Chang et al., "Germ Line Chimera Produced by Transfer of Cultured Chick Primordial Germ Cells," Cell Biology International, vol. 19, pp. 569-576 (1995).

Bresler et al., "Manipulations of Germ-Cell Populations in the Gonad of the Fowl," British Poultry Science, vol. 35, pp. 241-247 (1994).

Allioli et al., "Use of Retroviral Vectors to Introduce and Express the β-Galactosidase Marker Gene in Cultured Chicken Primordial Germ Cells," Developmental Biology, vol. 165, pp. 30-37 (1994).

Naito et al., "Production of Germline Chimeric Chickens, with High Transmission Rate of Donor-Derived Gametes, Produced by Transfer of Primordial Germ Cells," Mol. Reprod. Dev., vol. 39, pp. 153-161 (1994).

Han et al., "Primordial Germ Cells in Aves," AJAS, vol. 7 (No. 4), pp. 459-466 (1994.).

Vick et al., "Transgenic birds from transformed primordial germ cells," Prot, R. Soc. Lond. B, vol. 251, pp. 179-182 (1993).

Petitte et al., "Assessment of Functional Gametes in Chickens after Transfer of Primordial Germ Cells," J. Reprod. Fert., vol. 92, pp. 225-229 (1991).

Simkiss et al., "Infection of Primordial Germ Cells with Defective Retrovirus and Their Transfer to the Developing Embryo," Proceedings of the 4th World Congress on Genetics Applied to Livestock Production., pp. 111-114, School of Animal and Microbial Sciences, University of Reading, Whiteknights, Reading, UK (1990).

Official Action corresponding to Chinese Patent Application No. 200480007059.8 dated May 8, 2009.

Chang et al., Proliferation of chick primordial germ cells cultured on stroma cells from the germinal ridge. Cell Biology International. vol. 19, No. 2 pp. 143-149 (1995).

Correspondence summarizing Notice of Allowance in related Mexican Patent Application No. PA/a/2005/007613 dated Nov. 21, 2008.

Correspondence summarizing Official Action in related Mexican Patent Application No. PA/a/2005/007613 dated May 4, 2008.

Correspondence summarizing Official Action in related Mexican Patent Application No. PA/a/2005/007613 dated Aug. 3, 2008.

Buehr, "The Primordial Germ Cells of Mammals: Some Current Perspectives," Exp. Cell Res., vol. 232, pp. 194-207 (1997).

Carsience et al., "Germline chimeric chickens from dispersed donor blastodermal cells and compromised recipient embryos," Development, vol. 117, pp. 669-675 (1993).

Cooke et al., "A murine homologue of the human DAZ gene is autosomal and expressed only in male and female gonads," Hum. Mol. Genet., vol. 5, pp. 513-516 (1996).

Etches et al., "Manipulation of Blastodermal Cells," Poult. Sci., vol. 76, p. 1075 (1997).

Ginsburg & Eyal-Giladi, "Temporal and spatial aspects of the gradual migration of primordial germ cells from the epiblast into the germinal crescent in the avian embryo," J. Embryol. Exp. Morphol., vol. 95, p. 53 (1986).

Hay et al., "A Protein Component of Drosophila Polar Granules Is Encoded by vasa and Has Extensive Sequence Similarity to ATP-Dependent Helicases," Cell, vol. 55, pp. 577-587 (1988).

Houston & King, "A critical role for Xdazl, a germ plasm-localized RNA, in the differentiation of primordial germ cells in Xenopus," Development, vol. 127, pp. 447-456 (2000).

Kagami et al., "The Developmental Origin of Primordial Germ Cells and the Transmission of the Donor-Derived Gametes in Mixed-Sex Germline Chimeras to the Offspring in the Chicken," Mol. Reprod. Dev., vol. 48, p. 501 (1997).

Karagenç et al., "Origin of Primordial Germ Cells in the Prestreak Chick Embryo," Dev. Genet., vol. 19, pp. 290-301 (1996).

Kimura et al., "Molecular Cloning and Genomic Organization of Mouse Homologue of Drosophila germ cell-less and Its Expression in Germ Lineage Cells," Biochem. Biophys. Res. Commun., vol. 262, pp. 223-230 (1999).

Lasko & Ashburner, "The product of the Drosophila gene vasa similar to eukaryotic initiation factor-4A," Nature, vol. 335, pp. 611-617 (1988).

Lee et al., "The role of the cell surface in the migration of primordial germ cells in early chick embryos: effects of concanavalin A," J. Embryol. Exp. Morph., vol. 46, p. 5 (1978).

Maeda et al., "Mortality, Size of the Gonads, and Ultrastructure of Primordial Germ Cell in Chick Embryos Treated with γ-Irradiation or Injected with Donor Cells," Poultry Sci., vol. 77, pp. 905-907 (1998).

Mita & Yamashita, "Gene expression pattern Expression of Xenopus Daz-like protein during gametogenesis and embryogenesis," Mech. Dev., vol. 94, pp. 251-255 (2000).

Mraz & Woody, "Egg Production in Hens Continuously Irradiated as Embryos," Radiation Res., vol. 54, pp. 63-68 (1973).

Swartz, "Response of Early Chick Embryos to Busulfan," Teratology, vol. 21, pp. 1-8 (1980).

Tajima et al., "Production of Germ-Line Chimeras by Transfer of Cryopreserved Gonadal Primordial Germ Cells (gPGCs) in Chicken," J. Exp. Zool., vol. 280, p. 265 (1998).

Watanabe et al., "Distribution analysis of transferred donor cells in avian blastodermal chimeras," Development, vol. 114, pp. 331-338 (1992).

Weidinger et al., "dead end, a Novel Vertebrate Germ Plasm Component, Is Required for Zebrafish Primordial Germ Cell Migration and Survival," Curr. Biol., vol. 13, pp. 1429-1434 (2003).

Xu et al., "A gene family required for human germ cell development evolved from an ancient meiotic gene conserved in metazoans," Proc. Natl. Acad. Sci. USA, vol. 98, pp. 7414-7419 (2001).

Communication regarding the expiry of the time limit within which notice of opposition may be filed corresponding to European Patent Application No. 04703077.0-2405 dated Jan. 22, 2009.

Issued Patent corresponding to Hong Kong Patent Application No. 06102558.4 dated Oct. 31, 2008.

Letter from Mexican patent attorney summarizing Notice of Allowance in related Mexican Patent Application No. PA/a/2005/007613 dated Nov. 21, 2008.

Letter from Mexican patent attorney summarizing Official Action in related Mexican Patent Application No. PA/a/2005/007613 dated May 4, 2008.

Letter from Mexican patent attorney summarizing Official Action in related Mexican Patent Application No. PA/a/2005/007613 dated Aug. 3, 2008.

Letter from Mexican patent attorney summarizing Issued Patent in related Mexican Patent Application No. PA/a/2005/007613 dated Jan. 14, 2009.

* cited by examiner

DEPLETION OF ENDOGENOUS
PRIMORDIAL GERM CELLS IN AVIAN
SPECIES

CROSS REFERENCE TO RELATED APPLICATION

This application claims the benefit of U.S. Provisional Patent Application Ser. No. 60/440,424, filed Jan. 16, 2003, the disclosure of which is incorporated herein by reference in its entirety.

TECHNICAL FIELD

The presently disclosed subject matter relates to methods for modulating primordial germ cell numbers in an avian. More particularly, the presently disclosed subject matter relates to the use of antibodies that bind to antigens associated with primordial germ cells to modulate the development of primordial germ cells during embryogenesis in avians. Donor primordial germ cells can be administered to avian embryos present within eggs produced by birds treated with the presently disclosed methods to create chimeric avians.

BACKGROUND ART

Chimeras are composite organisms comprising cells derived from more than one zygote. Experimental chimeras have been used to study cell-to-cell interactions and perform cell fate and lineage analyses during development (McLaren, *Mammalian Chimeras*. Cambridge University Press, Cambridge, England, United Kingdom, 1976). The use of cells isolated from very early embryos to produce chimeras can result in organisms that develop with a full complement of somatic tissues partially made up of descendents of the isolated cells. If the starting material includes early germ cells or their precursors, the resulting chimeras can produce gametes of both the donor and recipient genotypes. In addition, chimeras can be intraspecific (i.e. containing cells derived from two or more zygotes of the same species) or interspecific (i.e. containing cells derived from zygotes from at least two different species).

The efficiency of generating germline chimeras by repopulating the gonads with the desired donor PGCs can be enhanced by reducing the number of PGCs in the recipient organism. A number of approaches to reduce PGCs have been utilized with varying degrees of success. Continuous exposure to gamma irradiation (0.3-3.4 R/hr of $^{60}$Co for 20 days) resulted in the complete destruction of oocytes at a dosage level of 3.4 and 1.8 R/hr (Mraz & Woody, *Radiation Res* 54:63-68, 1973). However, hatching frequency was reduced at levels of 0.9 R/hr or higher. The application of continuous low-level gamma irradiation to reduce endogenous PGC numbers is limited due to the relatively small numbers of eggs that can be exposed at any one time, the long period of exposure required, and also the potentially teratogenic effects of the irradiation itself.

Short-term exposure to a gamma source has also been attempted (Carsience et al., *Development* 117:669-75, 1993; Thoraval et al., *Poultry Sci* 73:1897-1905, 1994; Maeda et al., *Poultry Sci* 77:905-07, 1998). In these studies, unincubated eggs were exposed to 500-700 rads just prior to the injection of stage X blastodermal or area pellucida cells. The incidence of germline chimerism following short-term gamma irradiation was highly variable. The basis for the inconsistent results was ascribed to "donor cells being injected into an inappropriate location . . ." (Carsience et al., *Development* 117:669-75, 1993).

Attempts to sterilize recipient embryos using ultraviolet (UV) light have also been described (Reynaud, *J Embryol Exp Morphol* 21:485-507, 1969; Reynaud, *J Roux's Arch Devel Biol* 179:85-110, 1976; Aige-Gil & Simkiss, *Br Poul Sci* 32:427-438, 1991). Aige-Gil & Simkiss concluded "it is not possible to irradiate the germinal crescent, particularly at stage 4 of incubation, without inducing major abnormalities". The degree of sterility appeared to be positively correlated with developmental abnormalities, thus limiting the practical use of UV-light as a means to reduce endogenous PGC.

The generation of germ line chimeras produces several potential benefits both to mankind and to the various avian species themselves. Germ line chimeras can be used as a source of gametes with desirable characteristics, which can then be used in conjunction with breeding programs to augment the avian gene pool. The ability to more easily produce gametes of particular avian species would be useful to the avian veterinary and poultry production fields. For endangered species such as the whooping crane, it would be extremely useful to have a ready supply of male spermatozoa. For commercial birds such as turkeys, it would be desirable to more quickly and economically produce male spermatozoa. For meat-producing flocks, it is desirable to have ways to increase the ratio of male birds in the flock. As such, there is a need for new ways to obtain avian spermatozoa.

Accordingly, there remains a long-felt and continuing need for ways to increase the efficiency of the production of germ line chimeras in avians. The presently disclosed subject matter addresses this and other needs in the art.

SUMMARY

The presently disclosed subject matter provides methods for modulating primordial germ cells numbers in an avian embryo. In one embodiment, the method comprises immunizing a female bird with an antigen associated with primordial germ cells, whereby an egg produced by the female bird comprises a sufficiently high concentration of antibodies specific for the antigen to modulate numbers of endogenous PGCs in an avian embryo present within in the egg. In one embodiment, the female bird is selected from the group consisting of chicken, turkey, duck, quail, and sand hill crane. In another embodiment, the female bird is a chicken. In one embodiment, the antigen comprises an epitope of a polypeptide selected from the group consisting of SSEA-1, VASA, EMA-1, germ cell-less, dead end, nanos, stella, fragilis, and DAZL. In one embodiment, the immunizing step results in a decrease in primordial germ cell numbers in the avian embryo. In another embodiment, the immunizing step results in an increase in primordial germ cell numbers in the avian embryo.

The presently disclosed subject matter also provides a method for modulating primordial germ cell development in an avian embryo. In one embodiment, the method comprises immunizing a female bird with an antigen associated with primordial germ cells, whereby an egg produced by the female bird comprises a sufficiently high concentration of antibodies specific for the antigen to modulate development of PGCs in an avian embryo present within the egg. In one embodiment, the antigen comprises an epitope of a polypeptide selected from the group consisting of SSEA-1, VASA, EMA-1, germ cell-less, dead end, nanos, stella, fragilis, and DAZL. In one embodiment, the female bird is selected from the group consisting of chicken, turkey, duck, quail, and sand hill crane. In another embodiment, the female bird is a chicken. In one embodiment, the immunizing step results in an inhibition of development of the primordial germ cells in the avian embryo. In another embodiment, the immunizing step results in an enhancement of development of the primordial germ cells in the avian embryo.

The presently disclosed subject matter also provides a method for producing a chimeric avian. In one embodiment, the method comprises (a) immunizing a female avian with an antigen associated with primordial germ cells; (b) producing an egg from the female bird, wherein the egg comprises a sufficiently high concentration of antibodies specific for the antigen to modulate PGC development, PGC numbers, or combinations thereof, in a recipient embryo present within the egg; and (c) administering donor PGCs to the recipient embryo in ovo to produce a chimeric avian. In one embodiment, the antigen comprises an epitope of a polypeptide selected from the group consisting of SSEA-1, VASA, EMA-1, germ cell-less, dead end, nanos, stella, fragilis, and DAZL. In one embodiment, the donor PGCs are from the same avian species as the recipient embryo. In another embodiment, the donor PGCs are from a different avian species as the recipient embryo. In one embodiment, the method further comprises incubating the chimeric avian to hatch.

n one embodiment of the instant method, the female avian is selected from the group consisting of chicken, turkey, duck, quail, and sand hill crane. In one embodiment, the donor PGCs are from an avian embryo selected from the group consisting of chicken, turkey, duck, quail, and whooping crane. In another embodiment, the donor PGCs carry a pair of male determinative (Z) chromosomes. In still another embodiment, the donor PGCs are selected from the group consisting of gonadal PGCs, blood PGCs, and germinal crescent PGCs.

In still another embodiment, the donor PGCs carry a female determinative (w) chromosome. In one embodiment, the administering is by in ovo injection. In one embodiment, the donor PGCs are administered when the recipient embryo is between about stage IX according to the Eyal-Giladi & Kochav staging system and about stage 30 according to the Hamburger & Hamilton staging system. In another embodiment, the donor PGCs are administered when the recipient embryo is after stage 14 according to the Hamburger & Hamilton staging system. In still another embodiment, the administering step is carried out by injecting the recipient embryo with blastodermal cells, and wherein the blastodermal cells differentiate into donor PGCs in the recipient embryo.

The presently disclosed subject matter also provides a method for increasing the proportion of male birds in a plurality of bird eggs. In one embodiment, the method comprises (a) immunizing a female bird with an antigen associated with primordial germ cells; (b) producing an egg from the female bird, whereby the egg comprises a sufficiently high concentration of antibodies specific for the antigen to modulate PGC development in a recipient female bird present within the egg; (c) administering male (ZZ) PGCs to the recipient female bird in ovo; (d) incubating the recipient female bird to hatch; (e) raising the recipient female bird to sexual maturity; and (f) producing from the recipient female bird a plurality of bird eggs, wherein the proportion of male birds in the plurality of bird eggs produced by the recipient female bird is higher than would have been obtained in the absence of administering the male (ZZ) PGCs to the recipient female bird in ovo. In one embodiment, the antigen comprises an epitope of a polypeptide selected from the group consisting of SSEA-1, VASA, EMA-1, germ cell-less, dead end, nanos, stella, fragilis, and DAZL. In one embodiment, the female avian is selected from the group consisting of chicken, turkey, duck, quail, and sand hill crane. In one embodiment, the donor PGCs are from the same avian species as the recipient embryo. In another embodiment, the donor PGCs are from a different avian species as the recipient embryo. In another embodiment, the PGCs are selected from the group consisting of gonadal PGCs, blood PGCs, and germinal crescent PGCs. In yet another embodiment, the donor PGCs are from an avian embryo selected from the group consisting of chicken, turkey, duck, quail, and whooping crane.

In one embodiment of the instant method, the administering is by in ovo injection. In another embodiment, the donor PGCs are administered when the recipient embryo is between about stage IX according to the Eyal-Giladi & Kochav staging system and about stage 30 according to the Hamburger & Hamilton staging system. In another embodiment, the donor PGCs are administered when the recipient embryo is after stage 14 according to the Hamburger & Hamilton staging system. In still another embodiment, the administering step is carried out by injecting the recipient embryo with blastodermal cells, and wherein the blastodermal cells differentiate into donor PGCs in the recipient female bird.

The presently disclosed subject matter also provides a method for producing avian gametes from a second avian species in a first avian species. In one embodiment, the method comprises (a) immunizing a female of the first avian species with an antigen associated with primordial germ cells, whereby an egg produced by the female comprises a sufficiently high concentration of antibodies specific for the antigen to modulate PGC development of a recipient bird of the first avian species present within the egg; (b) introducing donor PGCs isolated from an avian of the second avian species into the recipient bird of the first avian species; (c) incubating the recipient bird of the first avian species to hatch; and (d) raising the recipient bird of the first avian species to sexual maturity, wherein the recipient bird of the first avian species produces gametes from the second avian species. In one embodiment, the antigen comprises an epitope of a polypeptide selected from the group consisting of SSEA-1, VASA, EMA-1, germ cell-less, dead end, nanos, stella, fragilis, and DAZL. In one embodiment, the first avian species and the second avian species are each selected from the group consisting of chicken, turkey, duck, quail, sand hill crane, and whooping crane. In one embodiment, the first avian species and the second avian species are the same. In another embodiment, the first avian species and the second avian species are different.

In one embodiment of the instant method, the administering is by in ovo injection. In one embodiment, the donor PGCs are administered when the recipient bird of the first avian species is between about stage IX according to the Eyal-Giladi & Kochav staging system and about stage 30 according to the Hamburger & Hamilton staging system. In another embodiment, the donor PGCs are administered when the recipient bird of the first avian species is after stage 14 according to the Hamburger & Hamilton staging system. In still another embodiment, the administering step is carried out by injecting the recipient bird of the first avian species with blastodermal cells, and wherein the blastodermal cells differentiate into donor PGCs in the recipient bird of the first avian species. In one embodiment, the PGCs are selected from the group consisting of gonadal PGCs, blood PGCs, and germinal crescent PGCs.

The presently disclosed subject matter also provides a method for enhancing germ line transmission of a nucleic acid molecule in a bird. In one embodiment, the method comprises (a) immunizing a female bird with an antigen associated with primordial germ cells, whereby an egg produced by the female bird comprises a sufficiently high concentration of antibodies specific for the antigen to modulate PGC development in a recipient bird present within the egg; (b) administering a plurality of donor PGCs comprising the nucleic acid molecule to the recipient bird under conditions sufficient to allow at least one of the plurality of PGCs to colonize a gonad of the recipient bird; (c) incubating the recipient bird to hatch; and (d) raising the recipient bird to sexual maturity, wherein the recipient bird produces gametes derived from the donor PGCs. In one embodiment, the antigen comprises an epitope of a polypeptide is selected from the group consisting of SSEA-1, VASA, EMA-1, germ cell-less, dead end, nanos, stella, fragilis, and DAZL. In one embodiment, the recipient bird and the donor PGCs are each selected from the group consisting of chicken, turkey, duck, quail, sand hill crane, and whooping crane. In one embodiment, the donor PGCs are from the same avian species as the recipient bird. In another embodiment, the donor PGCs are from a different avian species as the recipient bird. In one embodiment, the PGCs are selected from the group consisting of gonadal PGCs, blood PGCs, and germinal crescent PGCs.

In one embodiment of the instant method, the donor PGCs are administered when the recipient bird is between about stage IX according to the Eyal-Giladi & Kochav staging system and about stage 30 according to the Hamburger & Hamilton staging system. In another embodiment, the donor PGCs are administered when the recipient bird is after stage 14 according to the Hamburger & Hamilton staging system. In another embodiment, the administering is by in ovo injection. In another embodiment, the administering step is carried out by injecting the recipient bird with blastodermal cells, and wherein the blastodermal cells differentiate into donor PGCs in the recipient bird.

These and other aspects of the presently disclosed subject matter will become evident upon reference to the following detailed description and attached drawings. In addition, reference is made herein to various publications. All of the patents (including published patent applications) and publications (including GENBANK® sequence references) that are cited herein are hereby incorporated by reference in their entireties to the same extent as if each were specifically stated to be incorporated by reference, to the extent that they supplement, explain, provide a background for or teach methodology, techniques, and/or compositions employed herein. Any inconsistency between these patents and publications and the present disclosure shall be resolved in favor of the present disclosure.

BRIEF DESCRIPTION OF THE DRAWINGS

FIGS. 1A-1D depict immunohistological analyses of the gonadal regions of stage 27 embryos produced by hens that had been immunized with peptides derived from the chicken VASA polypeptide. Each section is stained with an antibody that is specific for SSEA-1.

FIG. 1A depicts sections from a control embryo produced by a hen that had not been immunized. FIG. 1B depicts sections from an embryo produced by a hen that had been immunized with a Vasa-C peptide (SEQ ID NO: 4). FIG. 1C depicts sections from a hen that had been immunized with a Vasa-N peptide (SEQ ID NO: 3). FIG. 1D depicts sections from an embryo produced by a hen that had been immunized with both the Vasa-N and the Vasa-C peptide (SEQ ID NOs: 3 and 4, respectively). SSEA-1+ cells (dark stained cells) are much more abundant in the control embryo (FIG. 1A) than in any of the embryos exposed to anti-VASA antibodies (FIGS. 1B-1D).

FIGS. 2A-2D depict immunohistological analyses of the gonadal regions of stage 27 embryos produced by hens that had been immunized with peptides derived from the chicken DAZL polypeptide. Each section is stained with an antibody that is specific for SSEA-1.

FIG. 2A depicts sections from a control embryo produced by a hen that had not been immunized. FIG. 2B depicts sections from an embryo produced by a hen that had been immunized with a DAZL-C peptide (SEQ ID NO: 8). FIG. 2C depicts sections from a hen that had been immunized with a DAZL-N peptide (SEQ ID NO: 7). FIG. 2D depicts sections from an embryo produced by a hen that had been immunized with both the DAZL-N and DAZL-C peptide (SEQ ID NOs: 7 and 8, respectively). SSEA-1+ cells (dark stained cells) are much more abundant in the control embryo (FIG. 2A) than in any of the embryos exposed to anti-DAZL antibodies (FIGS. 2B-2D).

FIGS. 3A and 3B depict immunohistological analyses of the gonadal regions of stage 27 embryos produced by hens that had been immunized with peptides derived from both the chicken Vasa and DAZL polypeptides. Each section is stained with an antibody that is specific for SSEA-1.

FIG. 3A depicts sections from a control embryo produced by a hen that had not been immunized. FIG. 3B depicts sections from an embryo produced by a hen that had been immunized with Vasa-N, Vasa-C, DAZL-N, and DAZL-C peptides (SEQ ID NOs: 3, 4, 7, and 8). SSEA-1+ cells (dark stained cells) are much more abundant in the control embryo (FIG. 3A) than in any of the embryos exposed to both anti-DAZL and anti-VASA antibodies (FIGS. 3B).

BRIEF DESCRIPTION OF THE SEQUENCE LISTING

Figure 1:
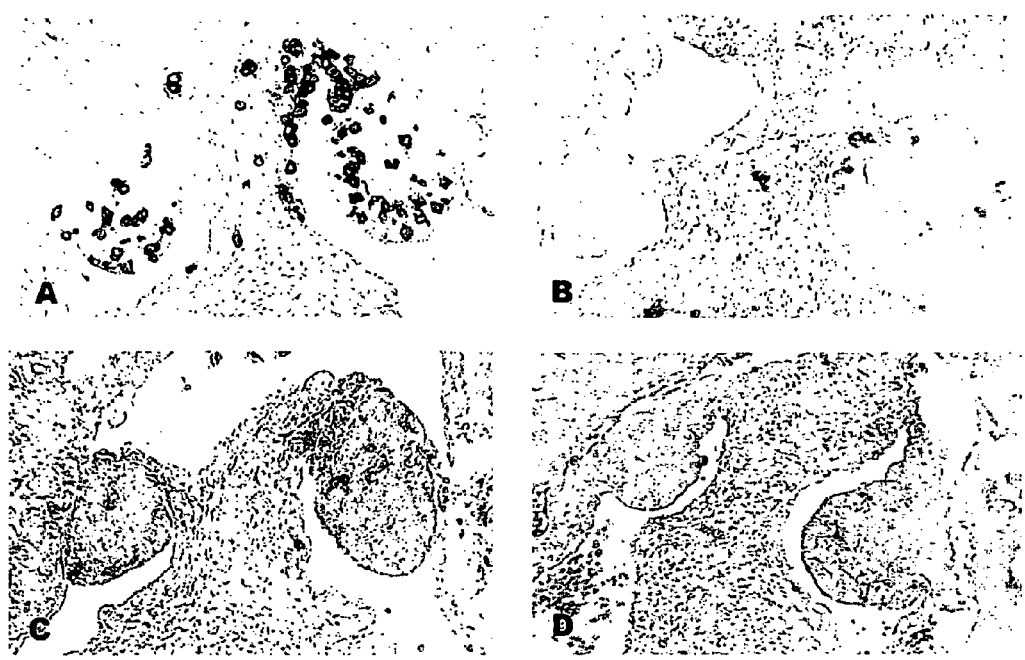
FIGS. 1-3 depict immunohistochemical analyses of the presence of SSEA-1+cells in chicken embryos exposed to antibodies raised against antigens associated with PGCs. For each Figure, cross sections of chicken embryos in the region of the developing gonads were stained using monoclonal antibody MC-480, which recognizes stage specific embryonic antigen-1 (SSEA-1) on primordial germ cells. Stage 27 embryos were fixed in 4% paraformaldehyde, paraffin sectioned at 7 μm, and immunostained with MC-480 and an alkaline phosphatase-conjugated secondary antibody. Positive staining was detected with NBT-BCIP enzyme substrate.

SEQ ID NOs: 1 and 2 are a nucleic acid and amino acid sequence, respectively, of a chicken VASA (CVH) open reading frame (GENBANK® Accession Nos. AB004836 and BAB12337, respectively).

SEQ ID NOs: 3 and 4 are the sequences of peptides comprising epitopes of a chicken VASA (CVH) polypeptide that were used to immunize female chickens. SEQ ID NO: 3 is an N-terminal peptide (Vasa-N) that corresponds to amino acids 42-57 of GENBANK® Accession No. BAB12337, and SEQ ID NO: 4 is a C-terminal peptide (Vasa-C) that corresponds to amino acids 645-660 of GENBANK® Accession No. BAB12337.

SEQ ID NOs: 5 and 6 are a nucleic acid and amino acid sequence, respectively, of a chicken DAZL open reading frame (GENBANK® Accession Nos. AY211387 and AAO26019, respectively).

SEQ ID NOs: 7 and 8 are the sequences of peptides comprising epitopes of a chicken DAZL polypeptide that were used to immunize female chickens. SEQ ID NO: 7 is an N-terminal peptide (Dazl-N) that corresponds to amino acids 2-18 of GENBANK® Accession No. AAO26019, and SEQ ID NO: 8 is a C-terminal peptide (DAZL-C) that corresponds to amino acids 266-282 of GENBANK® Accession No. AAO26019.

DETAILED DESCRIPTION

I. Definitions

Unless otherwise defined, all technical and scientific terms used herein have the same meaning as commonly understood by one of ordinary skill in the art to which the presently disclosed subject matter pertains. For clarity of the present specification, certain definitions are presented hereinbelow.

Following long-standing patent law convention, the terms "a" and "an" mean "one or more" when used herein, including in the claims.

As used herein, the term "about", when referring to a value or to an amount of mass, weight, time, volume, concentration or percentage is meant to encompass variations of ±20% or ±10%, in another example ±5%, in another example ±1%, and in still another example ±0.1% from the specified amount, as such variations are appropriate to practice the presently disclosed subject matter. Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

In certain embodiments, the presently disclosed subject matter employs antibodies against antigens associated with primordial germ cells. The term "antibody", and grammatical variations thereof, refers to immunoglobulin molecules and immunologically active portions of immunoglobulin molecules; i.e., molecules that contain an antigen-binding site that specifically bind an antigen. As such, the term refers to immunoglobulin proteins, or functional portions thereof, including polyclonal antibodies, monoclonal antibodies, chimeric antibodies, hybrid antibodies, single chain antibodies (e.g., a single chain antibody represented in a phage library), mutagenized antibodies, humanized antibodies, and antibody fragments that comprise an antigen binding site (e.g., Fab and Fv antibody fragments). Thus, "antibodies" include, but are not limited to monoclonal, chimeric, recombinant, synthetic, semi-synthetic, or chemically modified intact antibodies having for example Fv, Fab, scFv, or F(ab)$_2$ fragments. The immunoglobulin molecules of the presently disclosed subject matter can be of any type (e.g., IgG, IgE, IgM, IgD, IgA and IgY), class (e.g., IgG1, IgG2, IgG3, IgG4, IgA1 and IgA2), or subclass of immunoglobulin molecule.

Avians produce antibodies that can localize in the yolk of eggs, and these antibodies are termed "IgY" (yolk antibodies, comprising mainly antibodies of the IgG type). See generally Bollen et al., *J Immunol Meth* 191:113-120, 1996; Schade et al. (eds.), *Chicken Egg Yolk Antibodies, Production and Application: IgY-Technology*, Springer Verlag, New York, N.Y., United States of America, 2000. In one embodiment, the antibodies of the presently disclosed subject matter are avian IgY antibodies. The antibodies of the presently disclosed subject matter can be from any avian origin. In some embodiments, the antibodies are chicken IgY antibodies.

The antibodies of the presently disclosed subject matter bind to an antigen associated with primordial germ cells. As used herein, the term "associated with primordial germ cells" refers to a antigens comprising an epitope that is either expressed by, or post-translationally attached to, a polypeptide expressed by a primordial germ cell (for example, a cell surface marker) or by a cell capable of influencing the migration and/or development of a primordial germ cell (for example, migration factors, growth factors, and polypeptides expressed by cells present in the microenvironment in which PGCs are present or develop). Such antigens include, but are not limited to epitopes present on an SSAE-1, ovomucin-like protein (OLP), Steel Factor (c-kit ligand), germ cell-less, dead end, VASA (including, but not limited to the chicken VASA homolog, CVH), DAZL, nanos, stella, and fragilis polypeptides, and the antigens recognized by the antibodies EMA-1, QH-1, FC10.2, S-FC10.2, NC-1, 2C9, QCR1, AGC5, AGC7, and AGC13. Reviewed in Tajima, *Avian Poultry Biol Rev* 13:15-20, 2002. See also Buehr, *Exp Cell Res* 232, 194-207, 1997; D'Costa & Petitte, *Intl J Devel Biol* 43:349-56, 1999; Urven et al., *Development* 103:299-304, 1988; Hay et al., *Cell* 55:577-587, 1988; Lasko & Ashburner, *Nature* 335:611-617, 1988; Raz, *Nature Genetics* 4:690-700, 2003; Houston & King, *Development* 127:447-56, 2000; Cooke et al., *Hum Mol Genet* 5:513-516, 1996; Kimura et al., *Biochem Biophys Res Commun* 262:223-30, 1999; Weidinger et al., *Curr Biol* 13:1429-34, 2003; and references therein.

As used herein, the terms "SSEA-1 antibody" and "anti-SSEA-1 antibody" are used interchangeably and refer to an antibody, in one embodiment an IgY antibody and in another embodiment a monoclonal antibody, which binds to the stage specific embryonic antigen-1 (SSEA-1; Buehr, *Exp Cell Res* 232, 194-207, 1997). SSEA-1 is a carbohydrate epitope determined by a galactose (β1→4) fucose (α1→3) N-acetylglucosamine linkage (Gooi et al., *Nature* 292:156-158, 1981). A monoclonal antibody to SSEA-1 was developed by the fusion of mouse myeloma cells with spleen cells from a mouse that had been immunized with F9 teratocarcinoma cells (Solter & Knowles, *Proc Natl Acad Sci USA* 75:5565-5569, 1978). SSEA-1 antibody is a known immunohistochemical marker for avian germ cells (Karagenc et al., *Dev Genet* 19:290-301, 1996). In one embodiment, an anti-SSEA-1 antibody is clone MC 480, which can be obtained from the Developmental Studies Hybridoma Bank, The University of Iowa, Iowa City, Iowa, United States of America.

As used herein, the terms "VASA antibody" and "anti-VASA antibody" are used interchangeably and refer to an antibody, in one embodiment an IgY antibody, which binds to an avian VASA polypeptide. VASA is an ATP-dependent RNA helicases that is a member of the DEAD-box (Asp-Glu-Ala-Asp; SEQ ID NO: 9) family. VASA and its orthologs are expressed in the germplasm of many species, including zebrafish (*Danio rerio*),*Drosophila melanogaster, Caenorhabditis elegans,* and has been identified in PGCs from other species, including *Xenopus laevis,* the mouse, and humans (reviewed in Raz, *Nature Genetics* 4:690-700, 2003). In these species, VASA and related polypeptides have been implicated in germ cell development, including pole PGC development, proliferation, and differentiation, as well as gametogenesis. Id. The nucleic acid and amino acid sequences of chicken VASA (also called CVH) can be found at GENBANK® Accession Nos. AB004836and BAB12337, respectively.

As used herein, the terms "DAZL antibody" and "anti-DAZL antibody" are used interchangeably and refer to an antibody, in one embodiment an IgY antibody, which binds to an avian DAZL polypeptide. Orthologs of DAZL have been isolated from several species, including zebrafish (*Danio rerio*), *Drosophila melanogaster, Caenorhabditis elegans*, and has been identified in PGCs from other species, including *Xenopus laevis*, the mouse, and humans (reviewed in Raz, *Nature Genetics* 4:690-700, 2003). The DAZL polypeptide (and orthologs thereof) is an RNA-binding protein that is expressed in the vegetal pole of the zebrafish egg and the germ plasma of *Xenopus*, as well as in the ovary and/or testis of several different organisms. Id. In *Xenopus*, mouse, and humans, DAZL is expressed in PGCs, and might be important for the development and survival of cells in the gonad of one or both sexes. See Raz, *Nature Genetics* 4:690-700, 2003; Xu et al., *Proc Natl Acad Sci USA* 98:7414-7419, 2001; Houston & King, *Development* 127:447-56, 2000; Mite & Yamashita, *Mech Dev* 94:251-255, 2000; Ruggiu et al., *Nature* 389:73-77, 1997; Reijo et al., *Nature Genetics* 10:383-393, 1995. The nucleic acid and amino acid sequences of chicken DAZL can be found at GENBANK® Accession Nos. AY211387 and AAO26019, respectively.

As used herein, the terms "bird" and "avian species" refer to any avian species, including but not limited to chicken, turkey, duck, geese, quail, pheasant, and ostrich. Any of numerous other species can be employed to carry out the presently disclosed subject matter, particularly when it is used for the conservation of endangered species such as the whooping crane (where the recipient species would be the sand hill crane).

As used herein and unless specifically modified, the term "egg" refers to an avian egg that contains a live embryonic bird. Thus, the term "egg" is intended to refer to a fertilized avian egg, in one embodiment an egg containing an avian embryo that is capable of undergoing normal embryogenesis.

As used herein, the terms "native" and "endogenous" refer to a cell or a nucleic acid that is naturally present in the embryo. As such, an "endogenous PGC" is a PGC that is present in an embryo that has developed directed from the fertilized egg without the introduction of exogenous or donor PGCs. Similarly, when used in the context of a polypeptide, a "native polypeptide" is a polypeptide that is encoded by a native gene of an untransformed avian.

As used herein, the term "naturally occurring" refers to an object that is found in nature as distinct from being artificially produced by man. For example, a polypeptide or nucleotide sequence that is present in an organism (including a virus) in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleic acid sequence is identical to an amino acid or nucleic acid sequence found in nature.

As used herein, the terms "nucleic acid" and "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action.

The term "operatively linked", when describing the relationship between two nucleic acid regions, refers to a juxtaposition wherein the regions are in a relationship permitting them to function in their intended manner. For example, a control sequence "operatively linked" to a coding sequence is ligated in such a way that expression of the coding sequence is achieved under conditions compatible with the control sequences, such as when the appropriate molecules (e.g., inducers and polymerases) are bound to the control or regulatory sequence(s). Thus, in one embodiment, the phrase "operatively linked" refers to a promoter connected to a coding sequence in such a way that the transcription of that coding sequence is controlled and regulated by that promoter. Techniques for operatively linking a promoter to a coding sequence are well known in the art; the precise orientation and location relative to a coding sequence of interest is dependent, inter alia, upon the specific nature of the promoter.

Thus, the term "operatively linked" can refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operatively linked. Techniques for operatively linking a promoter region to a nucleotide sequence are known in the art. The term "operatively linked" can also refer to a transcription termination sequence or other nucleic acid that is connected to a nucleotide sequence in such a way that termination of transcription of that nucleotide sequence is controlled by that transcription termination sequence. Additionally, the term "operatively linked" can refer to a enhancer, silencer, or other nucleic acid regulatory sequence that when operatively linked to an open reading frame modulates the expression of that open reading frame, either in a positive or negative fashion.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

As used herein, the terms "primordial germ cell" and "PGC" refer to a diploid cell that is present in the early embryo and that can differentiate/develop into haploid gametes (i.e. spermatozoa and ova) in an adult bird. Primordial germ cells can be isolated from different developmental stages and from various sites in a developing avian embryo as is known to those of skill in the art including, but not limited to the genital ridge, the developing gonad, the blood, and the germinal crescent. See e.g. Chang et al., *Cell Biol Int* 21:495-9, 1997; Chang et al., *Cell Biol Int* 19:143-9, 1995; Allioli et al., *Dev Biol* 165:30-7, 1994; Swift, *Am J Physiol* 15:483-516; and PCT International Publication No. WO 99/06533. The genital ridge is a section of a developing embryo that is known to a person of ordinary skill in the art. See e.g., Strelchenko, *Theriogenology* 45: 130-141, 1996; Lavoir, *J Reprod Dev* 37: 413-424, 1994. Typically, PGCs are stain positively in the periodic acid-Schiff (PAS) technique. In several species, PGCs can be identified using an anti-SSEA antibody (one notable exception being turkeys, the PGCs from which do not display the SSEA antigen). Various techniques for isolation and purification of PGCs are known in the art, including the concentration of PGCs from blood using Ficoll density gradient centrifugation (Yasuda et al., *J Reprod Fertil* 96:521-528, 1992).

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In one embodiment, a method of the presently disclosed subject matter employs a RNA polymerase III promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR; Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues and cell types but are inactive in others. Exemplary tissue-specific promoters include those promoters described in more detail hereinbelow, as well as other tissue-specific and cell-type specific promoters known to those of skill in the art.

When used in the context of a promoter, the term "linked" as used herein refers to a physical proximity of promoter elements such that they function together to direct transcription of an operatively linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element. In one embodiment, a transcriptional regulatory sequence is a transcription termination sequence, alternatively referred to herein as a transcription termination signal.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. In one example, a p-value less than or equal to 0.05, in another example less than 0.01, in another example less than 0.005, and in yet another example less than 0.001, are regarded as significant.

The term "regulatory sequence" is a generic term used throughout the specification to refer to polynucleotide sequences, such as initiation signals, enhancers, regulators, promoters, and termination sequences, which are necessary or desirable to affect the expression of coding and non-coding sequences to which they are operatively linked. Exemplary regulatory sequences are described in Goeddel, 1990, and include, for example, the early and late promoters of simian virus 40 (SV40), adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences can differ depending upon the host organism. In prokaryotes, such regulatory sequences generally include promoter, ribosomal binding site, and transcription termination sequences. The term "regulatory sequence" is intended to include, at a minimum, components whose presence can influence expression, and can also include additional components whose presence is advantageous, for example, leader sequences and fusion partner sequences.

In certain embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide.

The term "reporter gene" refers to a nucleic acid comprising a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters. Generally, a reporter gene encodes a polypeptide not otherwise produced by the host cell, which is detectable by analysis of the cell(s), e.g., by the direct fluorometric, radioisotopic or spectrophotometric analysis of the cell(s) and typically without the need to kill the cells for signal analysis. In certain instances, a reporter gene encodes an enzyme, which produces a change in fluorometric properties of the host cell, which is detectable by qualitative, quantitative, or semiquantitative function or transcriptional activation. Exemplary enzymes include esterases, β-lactamase, phosphatases, peroxidases, proteases (tissue plasminogen activator or urokinase) and other enzymes whose function can be detected by appropriate chromogenic or fluorogenic substrates known to those skilled in the art or developed in the future.

As used herein, the term "transcription factor" refers to a cytoplasmic or nuclear protein which binds to a gene, or binds to an RNA transcript of a gene, or binds to another protein which binds to a gene or an RNA transcript or another protein which in turn binds to a gene or an RNA transcript, so as to thereby modulate expression of the gene. Such modulation can additionally be achieved by other mechanisms; the essence of a "transcription factor for a gene" pertains to a factor that alters the level of transcription of the gene in some way. The term "transcription factor" can also generally refer to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The term "vector" refers to a nucleic acid capable of transporting another nucleic acid to which it has been linked. One type of vector that can be used in accord with the presently disclosed subject matter is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

The term "expression vector" as used herein refers to a DNA sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross over oligonucleotide. For indirect recombination, no more than one of the sequences is an actual substrate for recombination, and in some cases, neither sequence is a substrate for recombination.

As used herein, the term "regulatory elements" refers to nucleotide sequences involved in controlling the expression of a nucleotide sequence. Regulatory elements can comprise a promoter operatively linked to the nucleotide sequence of interest and termination signals. Regulatory sequences also include enhancers and silencers. They also typically encompass sequences required for proper translation of the nucleotide sequence.

As used herein, the term "significant increase" refers to an increase in an mount (for example, a number of PGCs) that is larger than the margin of error inherent in the measurement technique, in one embodiment an increase by about 10% or greater over a baseline amount (for example, the average number of PGCs present at a specific location at a specific stage of development in an untreated, wild-type embryo), in another embodiment an increase by about 25% or greater, and in still another embodiment an increase by about 50% or greater.

As used herein, the terms "significantly less" and "significantly reduced" refer to an amount (for example, a number of PGCs) that is reduced by more than the margin of error inherent in the measurement technique, in one embodiment a decrease by about 10% or greater with respect to a baseline amount (for example, the average number of PGCs present at a specific location at a specific stage of development in an untreated, wild-type embryo), in another embodiment, a decrease by about 25% or greater, and in still another embodiment a decrease by about 50% or greater.

As used herein, the term "specific binding", and grammatical variants thereof, refers to an affinity of binding that an antibody has to a cognate epitope. With respect to the disclosed methods, "specific binding" is intended to encompass a binding between an antibody (for example, an IgY molecule) and an antigen under physiological conditions (for example, within a location wherein PGCs can be found in an avian embryo) that results in a modulation of the normal biological activity of the macromolecule comprising the epitope. Stated another way, in one embodiment, an interaction between an IgY molecule and an epitope is considered specific if a biological activity of the macromolecule to which the IgY molecule binds in a developing embryo is altered relative to the activity of the macromolecule in another developing embryo at a similar stage in the absence of the IgY molecule.

As such, the phrases "specifically (or selectively) binds to an antibody" and "specifically immunoreactive with", when referring to an epitope present on a polypeptide or peptide, refer to a binding reaction which is determinative of the presence of the polypeptide in the presence of a heterogeneous population of polypeptides and other biologics. Thus, under designated immunoassay conditions, the specified antibodies bind to a particular polypeptide and do not bind in a significant amount to other polypeptides present in the sample. Specific binding to an antibody under such conditions can require an antibody that is selected for its specificity for a particular polypeptide. For example, antibodies raised to an antigen associated with PGCs can be selected to obtain antibodies specifically immunoreactive with that antigen and not with other antigens. A variety of immunoassay formats can be used to select antibodies specifically immunoreactive with a particular polypeptide. For example, solid phase ELISA immunoassays, Western blots, or immunohistochemistry are routinely used to select monoclonal antibodies specifically immunoreactive with a polypeptide. See Harlow & Lane, *Antibodies: A Laboratory Manual*, Cold Spring Harbor Laboratories, Cold Spring Harbor, N.Y., United States of America, 1988, for a description of immunoassay formats and conditions that can be used to determine specific immunoreactivity. Typically a specific or selective reaction will be at least twice background signal or noise and more typically more than 10 to 100 times background.

As used herein, the term "transformation" refers to a process for introducing heterologous DNA into an avian cell, avian tissue, or avian. Transformed avian cells, avian tissue, and avians are understood to encompass not only the end product of a transformation process, but also transgenic progeny thereof.

As used herein, the terms "transformed", "transgenic", and "recombinant" refer to a host organism such as an avian PGC into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or cells are understood to encompass not only the end product of a transformation process, but also transgenic progeny thereof. A "non-transformed," "non-transgenic", or "non-recombinant" host refers to a wild-type organism, e.g., a wild-type avian PGC, which does not contain the heterologous nucleic acid molecule.

II. Immunizing Birds and the Deposition of Antibodies in Egg Yolk

Avians, in particular chickens, have become an increasingly common source of large-scale production of polyclonal antibodies due to the fact that large amounts of antibodies are transferred from serum to the yolk of eggs during egg production. See Rose et al., *Eur J Immunol* 4:521, 1974. The presently disclosed subject matter takes advantage of this phenomenon to effect PGC development in embryos by immunizing female avians with antigens associated with PGCs, which collect in the yolk. These antibodies can then bind to their cognate antigens during avian embryogenesis, thereby affecting the biological activities of polypeptides associated with PGC development.

A. Antigens and Epitopes

The presently disclosed subject matter encompasses polypeptides comprising, or alternatively consisting of, epitopes of the polypeptide that can be used to generate IgY antibodies that bind to the epitopes. In alternative, non-limiting embodiments, the polypeptides comprise an amino acid sequence of SEQ ID NOs: 2 or 6, and the epitopes are present on peptide antigens having an amino acid sequence of SEQ ID NOs: 3, 4, 7, or 8. It should be noted, however, that the peptide antigens disclosed herein as Vasa-N, Vasa-C, Dazl-N, and Dazl-C are intended to be representative only, and other antigenic peptides and polypeptides, including the full length version of a polypeptide associated with PGC development (including, but not limited to a polypeptide comprising an amino acid sequence presented in SEQ ID NOs: 2 or 6) can be used as immunogens.

The term "epitopes", as used herein, refers to portions of a polypeptide that have antigenic or immunogenic activity in an avian, in one embodiment a chicken. In one embodiment, the presently disclosed subject matter encompasses a polypeptide comprising an epitope, as well as the polynucleotide encoding this polypeptide. An "immunogenic epitope", as used herein, is defined as a portion of a protein that elicits an antibody response in an avian, as determined by any method known in the art, for example, by the methods for generating antibodies described herein. The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic. It is to be understood that as used herein, the term epitope encompasses any portion of a polypeptide that has antigenic or immunogenic activity in an avian including, but not limited to a subset of the amino acids of the polypeptide itself (also referred to herein as a "peptide antigen"), but also including any modifications of the polypeptide that incorporate additional moieties into the polypeptide (for example, the post-translational addition of one or more carbohydrate groups).

Fragments that function as epitopes can be produced by any conventional approach. See e.g., Houghten, *Proc Natl Acad Sci USA* 82:5131-5135, 1985; further described in U.S. Pat. No. 4,631,211.

In the presently disclosed subject matter, antigenic epitopes contain a sequence of in one embodiment at least 4, in another embodiment at least 5, in another embodiment at least 6, in another embodiment at least 7, in another embodiment at least 8, in another embodiment at least 9, in another embodiment at least 10, in another embodiment at least 15, in another embodiment at least 20, in another embodiment at least 25, and in still another embodiment between about 15 to about 30 amino acids. Representative polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including IgY antibodies, which specifically bind the epitope. Antigenic epitopes can be used as the target molecules in immunoassays. See e.g., Wilson et al., *Cell* 37:767-778, 1984; Sutcliffe et al., *Science* 219:660-666, 1983.

Similarly, immunogenic epitopes can be used, for example, to induce antibodies according to methods well known in the art. See e.g., Sutcliffe et al., supra; Wilson et al., supra; Chow et al., *Proc Natl Acad Sci USA* 82:910-914, 1985; and Bittle et al., *J Gen Virol* 66:2347-2354, 1985. The polypeptides comprising one or more immunogenic epitopes can be presented for eliciting an antibody response together with a carrier protein, such as an albumin, to an avian system (such as, for example, chicken), or, if the polypeptide is of sufficient length (at least about 25 amino acids), the polypeptide can be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the presently disclosed subject matter can be used to induce antibodies according to methods well known in the art including, but not limited to, in vivo immunization. See e.g., Sutcliffe et al., supra; Wilson et al., supra; and Bittle et al., supra. If in vivo immunization is used, avians can be immunized with free peptide; however, anti-peptide antibody titer may be boosted by coupling the peptide to a macromolecular carrier, such as keyhole limpet hemacyanin (KLH), bovine serum albumin (BSA), or tetanus toxoid. For instance, peptides containing cysteine residues can be coupled to a carrier using a linker such as maleimidobenzoyl-N-hydroxysuccinimide ester (MBS), while other peptides can be coupled to carriers using a more general linking agent such as glutaraldehyde. Avians such as, for example, chickens, are immunized with either free or carrier-coupled peptides, for instance, by intramuscular injection (for example, into the pectoralis major) of emulsions containing about 10-1000 micrograms of peptide or carrier protein and Freund's adjuvant or any other adjuvant known for stimulating an immune response. Several booster injections can be employed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal can be increased by selection of anti-peptide antibodies, for instance, by adsorption to the peptide on a solid support and elution of the selected antibodies according to methods well known in the art.

B. Conjugates and Adjuvants

As is well known in the art, a given composition may vary in its immunogenicity. It is often necessary therefore to boost the host immune system, as may be achieved by conjugating a peptide or polypeptide immunogen to a carrier. Representative carriers are keyhole limpet hemocyanin (KLH) and bovine serum albumin (BSA). Other albumins such as ovalbumin, mouse serum albumin, or rabbit serum albumin can also be used as carriers. Methods for conjugating a polypeptide to a carrier protein are well known in the art and include the use of glutaraldehyde, m-maleimidobenzoyl-N-hydroxysuccinimide ester, carbodiimide, and bis-biazotized benzidine.

As is also well known in the art, the immunogenicity of a particular immunogen composition can be enhanced by the use of non-specific stimulators of the immune response, known as adjuvants. Representative adjuvants include complete Freund's adjuvant (a non-specific stimulator of the immune response containing killed *Mycobacterium tuberculosis*), incomplete Freund's adjuvant, aluminum hydroxide, and TITERMAX® adjuvant (TMA; CytRx Corp., Norcross, Ga., United States of America).

The amount of immunogen composition used in the production of polyclonal antibodies varies upon the nature of the immunogen as well as the animal used for immunization. A variety of routes can be used to administer the immunogen (subcutaneous, intramuscular, intravenous and intraperitoneal). In one embodiment, avians are immunized by intramuscular injection of an antigen preparation into the pectoralis major muscle. The production of polyclonal antibodies can be monitored by sampling blood of the immunized animal at various points following immunization. Subsequent, booster injections can also be given. The process of boosting and titering is repeated until a suitable titer is achieved. When a desired level of immunogenicity is obtained, the immunized animal can be bled and the serum isolated and stored.

C. Isolation of Antibodies from Yolk

Antibodies that bind to antigens associated with PGCs are deposited in the yolk of eggs produced by female birds immunized with the antigens (for example, with peptides comprising the antigens). In some embodiments, antibodies can be isolated from the yolk using techniques known to those of skill in the art. See e.g. Akita et al., *J Immunol Meth* 160:207-214, 1993; Akita et al., *J Food Sci* 57:629-634, 1992; U.S. Pat. No. 4,357,272. As taught in U.S. Pat. No. 4,357,272, IgY can be purified from yolk by precipitation with polyethylene glycol (PEG). Briefly, yolks can be collected and washed in distilled water to remove albumen. Yolks can be passed through a glass funnel into a measuring cylinder, which causes the yolk sacs to break and releases the yolk, which collects in the cylinder. The volume of yolk is measured and a volume of buffer (for example, phosphate buffered saline; PBS) equivalent to two volumes of yolk is added and thoroughly mixed. PEG (for example, PEG 6000) is added to a final concentration of 3.5% (weight:volume; w:v). The mixture is stirred until the PEG is completely dissolved. The mixture is then centrifuged at 12,000 g for ten minutes. The centrifugation step results in the production of three phases in the centrifuge tubes. The top layer is a yellow fatty layer, the middle layer is a clear supernatant layer, and a bottom layer consisting of the bulk of the yolk and a protein "pellet". The IgY-containing supernatant fluid and the fatty layer can be decanted into a funnel containing an absorbent cotton plug in the neck of the funnel. The plug removes the lipid layer. The volume of the clear filtrate is then measured and PEG added by gentle stirring to a final concentration of 12 g PEG per 100 ml yolk extract. At this concentration the PEG causes complete displacement of the IgY. The precipitate is then centrifuged as before. The pellets can be redissolved to the original volume in phosphate buffer and the IgY once more precipitated with 12% PEG and centrifuged. Residual PEG can be removed by two rounds of re-centrifugation and aspiration of any liquid (IgY being found in the pellet). Thereafter, the final pellets can be dissolved in a volume of phosphate buffer equivalent to half the volume of yolk from which it was derived, although by dissolving the pellets in a smaller volume, more concentrated solutions can be obtained if desired. For injection into animals where a more complete removal of PEG is desirable, the IgY can be freed of traces of PEG by precipitation of the IgY with half saturated ammonium sulfate followed by centrifugation. The PEG forms a liquid phase in the aqueous ammonium sulfate phase, while the IgY forms a third phase on the bottom of the centrifuge tube.

IgY purified by this, or any other method known to those in the art, can be used in immunoassays including, but not limited to enzyme-linked immunosorbent assays (ELISAs), immunoprecipitation, etc., using techniques that are known in the art. Standard secondary reagents, such as anti-IgY secondary antibodies, are available from a number of manufacturers, including Research Diagnostics Inc., Flanders, N.J., United States of America, and Aves Labs, Inc., Tigard, Oreg., United States of America.

III. Methods of Modulating PGC Proliferation and Development

The presently disclosed subject matter provides methods for modulating PGC development in an avian embryo. The modulation provided by the disclosed methods can take the form of either a qualitative or quantitative difference in the PGCs of the embryo, including but not limited to a reduction or an enhancement of the number of PGCs present in the developing embryo relative to the number of PGCs normally found in a same stage embryo of the same species that has not been exposed to the methods described herein. Alternatively, the modulation can take the form of interference with the normal development of PGCs in the embryo such that the PGCs fail to develop normally, either in terms of migration to the gonad or in terms of their development once they enter the microenvironment of the embryonic gonad.

Several groups have reported the use of chemicals or radiation to modulate the level of PGCs in avian embryos. One particular chemical that has been used to reduce endogenous PGCs levels is busulfan (see Aige-Gil & Simkiss, *Res Vet Sci* 50:139, 1991; Vick et al., *J Reprod Fert* 98:637; Bresler et al., *Br Poutry Sci* 35:241, 1994; Hallett & Wentworth, *Poultr Sci* 70:1619, 1991; U.S. Patent Application Publication No. 20030111016). The compound busulfan (1,4-butanediol dimethane sulfonate, BU) has been used as a chemotherapeutic agent in the treatment of leukemia (Bhagwatwar et al., *Cancer, Chemother Pharmacol* 37:401-08, 1996). In 1963, Hemsworth and Jackson demonstrated that the administration of BU in rats could markedly impair the development of PGCs (Hemsworth & Jackson, *J Reprod Dev* 6:229-33, 1963). Injection of BU into the yolk sac of chick embryos resulted in multiple malformations (Swartz, *Teratology* 21:1-8, 1980). Hallett and Wentworth (*Poult Sci* 70:1619-23, 1991) also reported significant declines in hatchability following injection of an albumen suspension of BU into quail eggs. In some BU treated quail, there appeared to be an absence of germ cells in the gonads, while other similarly treated birds appeared normal. The authors suggested that "inconsistencies in the delivery of BU to the embryo" might explain the observed variation. They concluded that discovering a non-toxic solvent system would be necessary to eliminate the inconsistent results associated with use of a suspension. Aige-Gil & Simkiss (*Br Poult Sci* 32:427-438, 1991) used saline or sesame oil suspensions of BU, or solublized BU in dimethyl sulphoxide (DMSO) in chick embryos. Administration of DMSO alone produced embryonic mortality, developmental delays, and malformations that exceeded those observed with saline. The teratogenic effects were greatly minimized when BU was suspended in sesame oil and injected into yolk. Injection of 100 μg BU in sesame oil resulted in a sterility index of 95+%. In a subsequent experiment, Vick and co-workers (*J Reprod Fertil* 98:637-41, 1993) reported that the injection of 25, 50, and 250 μg BU significantly reduced gonadal germ cells in chick embryos. They estimated that BU treatment increased the rate of germline chimerism 3.5-fold when compared to non-BU treated embryos. Bresler et al. (*Br Poult Sci* 35:241-47, 1994) demonstrated that treatment with BU and subsequent injection of PGCs could result in a significant repopulation of the gonad. Injection of 50 μg BU, suspended in sesame oil reduced PGCs in the left and right gonad of 6 day-old chick embryos by 75 and 78%, respectively. Following the injection of a suspension of germinal crescent cells into BU-treated embryos, PGC numbers increased to 72 and 115% of controls for the left and right gonad, respectively. The variability in delivery of BU to the gonad, and the resulting inconsistency in the effectiveness in reducing the number of PGCs, limits the usefulness of this technology.

In U.S. Patent Application Publication No. 20030111016, the present co-inventors used of busulfan to reduce endogenous PGCs prior to administering donor PGCs. Briefly, fifteen mg of busulfan was dissolved in 5 ml of dimethyl formamide (DMF) in a glass vial. Five ml of sesame oil was added to the solution. The mixture was vortexed completely to create an emulsion. The concentration of busulfan was 1.5 μg/μl in the emulsion. Fresh busulfan emulsion was prepared for each batch of injections. Fertilized eggs were incubated at 37.5° C., 60% relative humidity for 22 hours. Then the eggs were placed horizontally in the incubator for 2 hours. The blunt end of each egg was cleaned with 70% ethanol. Using a curved forceps, a small hole was then made in the shell covering the air chamber, without damaging the outer shell membrane. Fifty μl of busulfan emulsion (containing 75 μg busulfan) was injected horizontally through the air chamber into the yolk using a hypodermic needle (21 G×1.5 inch). The emulsion was vortexed completely before use. The eggs were kept horizontal for the entire injection procedure. The hole in the shell was sealed with scotch tape. The eggs were incubated vertically after injection.

Busulfan-treated embryos were collected at stage 27 (H&H) and fixed in 4% paraformaldehyde. The embryos were embedded in paraffin, sectioned at 7 μm thickness, and stained immunohistochemically with SSEA-1 antibody. The number of PGCs in the left and right gonad in 10 randomly selected sections from each embryo was counted, and the index of sterility (IS) was calculated using the equation IS= (N−X)/N where N is the PGC number from control gonads and X is the PGC number from busulfan treated embryo (Reynaud, *J Embryol Exp Morphol* 21:485-507, 1969). The effects of treatment with sesame oil, DMF, and busulfan on survivability of chick embryos to Stage 27 was determined, and hatchability of treated birds following administration of busulfan was also assessed. Busulfan was shown to reduce PGCs numbers, particularly at a dose of 75 μg emulsified in sesame oil and DMF, although survivability of the treated embryos was one-quarter to one-half that seen in uninjected controls.

In some embodiments, the presently disclosed subject matter provides a method for modulating primordial germ cells numbers in an avian embryo, the method comprising immunizing a female bird with an antigen associated with primordial germ cells, whereby an egg produced by the female bird comprises a sufficiently high concentration of antibodies specific for the antigen to modulate numbers of endogenous PGCs in an avian embryo present within in the egg.

As used herein, the term "modulate" refers to an increase, decrease, or other alteration of any, or all, chemical and biological activities or properties of a biochemical entity, e.g., a PGC. As such, the term "modulate" can refer to a change in the numbers of PGCs present in the developing embryo relative to non-chimeric embryos of the same species at the same stage. For example, the term "modulate" can mean "inhibit", "reduce", or "suppress", but the use of the word "modulate" is not limited to this definition.

As used herein, the terms "inhibit", "reduce", "suppress", "down regulate", and grammatical variants thereof are used interchangeably and refer to an activity whereby the number or development of PGCs present in an embryo is reduced below that observed in the absence of antibodies directed against an antigen present on a polypeptide associated with PGCs. In one embodiment, inhibition with an antibody molecule (for example, an IgY directed against VASA, DAZL, EMA-1, etc.) results in a decrease in the number of PGCs present in the embryo prior to repopulation with donor PGCs.

In another embodiment, the number of PGCs present in an avian embryo is greater in the presence of antibodies directed against an antigen present on a polypeptide associated with PGCs than in their absence.

The term "modulation" as used herein refers to both upregulation (i.e., activation, enhancement, or stimulation) and downregulation (i.e., inhibition, reduction, or suppression) of the number of PGCs (or the development thereof) in the embryo prior to repopulation with donor PGCs. Thus, the term "modulation", when used in reference to a functional property or biological activity or process (e.g., the development, including but not limited to the proliferation, of PGCs) refers to the capacity to upregulate (e.g., activate, enhance, or stimulate), downregulate (e.g., inhibit, reduce, or suppress), or otherwise change a quality of such property, activity, or process (for example, PGC development and proliferation).

In particular embodiments of the presently disclosed subject matter, the number of endogenous PGCs in the recipient bird is reduced prior to introduction of the donor PGCs. In this manner, the donor PGCs can repopulate the gonads of the recipient bird and can increase the efficiency of producing chimeric birds and the proportion of gametes (and offspring) that are derived from the donor bird. The endogenous PGCs can be reduced by at least about 10%, 20%, 30%, 40%, 50%, 60%, 70%, 80%, 90%, 95%, 98% or even more. In other particular embodiments, the recipient bird is essentially sterilized, as that term is defined herein. The targeted reduction in endogenous PGC number in the recipient bird can be based on a number of considerations, including, but not limited to the desired number and proportion of gametes to be derived from the donor bird, minimization of any adverse effects associated with the method of achieving endogenous PGC reduction, and the like.

Alternatively stated, the presently disclosed methods can be practiced so that the ratio of gametes (and/or offspring) derived from the donor PGCs as compared with the recipient bird's PGCs may be about 10/90, 20/80, 30/70, 40/60, 50/50, 60/40, 70/30, 80/20, 90/10, or higher. In some embodiments, the methods of the presently disclosed subject matter can be practiced so that fewer than 50% of the gametes (and/or offspring) are derived from the donor PGCs. A relatively low proportion of gametes and/or offspring derived from donor PGCs can be acceptable in those applications in which only a relatively small number of donor gametes and/or offspring from chimeric birds are necessary and/or the donor gametes and/or offspring from chimeric birds are commercially valuable.

In one embodiment, PGC numbers in the recipient bird are reduced as a result of the presence of maternal antibodies deposited in the yolk of the egg. These antibodies, generally referred to as IgY, are capable of influencing the development of PGCs in the embryo when they bind to antigens present on polypeptides associated with PGCs, in one embodiment antigens that are present on polypeptides that are associated with PGC migration or development.

The reduction in PGCs is achieved by immunizing a female bird with an antigen associated with PGCs. The antigen can be present on a polypeptide associated with PGCs development (for example, a VASA polypeptide), including but not limited to a peptide antigen (for example, a stretch of 4 or more amino acids of a VASA polypeptide) and a carbohydrate antigen (for example, a carbohydrate moiety post-translationally added to polypeptide on the surface of a PGC). When a female bird is immunized with such an antigen (or a plurality of antigens), the bird can generate an immune response to the antigen. When an immunized bird produces an egg, antibodies to the antigen are deposited into the yolk of the egg. Those antibodies are then capable of binding to their cognate antigens present in the embryo developing in the egg, thereby modulating a biological activity of macromolecules present within the developing embryo that contain the antigen.

IV. Methods of Producing Chimeric Avians

The presently disclosed subject matter also provides a method for producing a chimeric avian. In some embodiments, the method comprises (a) immunizing a female avian with an antigen associated with primordial germ cells; (b) producing an egg from the female bird, wherein the egg comprises a sufficiently high concentration of antibodies specific for the antigen to modulate PGC development, PGC numbers, or combinations thereof, in a recipient embryo present within the egg; and (c) administering donor PGCs to the recipient embryo in ovo to produce a chimeric avian.

Chimeric avians have been produced by transferring donor blastodermal cells into a recipient avian blastoderm. Reviewed in Etches et al., *Poult Sci* 76:1075, 1997. Chimeric avians, particularly germ line chimeras, have also been produced by transfer of PGCs into recipient embryos, including PGCs derived from germinal crescent, circulating PGCs found in blood, and gonadal PGCs found in the genital ridge. Reviewed in Tajima, *Avian Poult Biol Rev* 13:15-30, 2002. It has been reported that blastodermal cells contain presumptive PGCs (Kagami et al., *Mol Reprod Dev* 48:501, 1997; Ginsburg & Eyal-Giladi, *J Embryol Exp Morphol* 95:53, 1986), which if true might explain the ability to generate germ line chimeric avians by blastodermal cell transfer. In some embodiments of the presently disclosed subject matter, blastodermal cells and/or PGCs can be introduced into developing avian embryos by techniques that are known in the art, including injection of cells into into the sinus terminalis, injection into the aorta, injection into the germinal crescent, injection into the embryonic coelom, etc.

The majority of avian chimera production has employed the chicken. See e.g. Naito et al., *Mol Reprod Dev* 39:153-161, 1994. The production of chimeric avians is not limited to chickens, however. Chimeras have also been produced in quail by transferring early blastodermal cells from the quail into quail embryos. See Ono et al., *Jpn Poult Sci* 31:119, 1994. Additionally, inter-specific chimeras have been produced by introducing quail blastodermal cells into the chicken blastoderm (Watanabe et al., *Development* 114:331-338, 1992) and by introducing dissociated turkey germinal crescent cells and/or PGCs into chick embryos (Reynaud, *J Exbryol Exp Morphol* 21:485-507, 1969; U.S. Pat. No. 6,354, 242; U.S. Patent Application Publication 20030111016).

Those skilled in the art will appreciate that the donor PGCs can be genetically modified prior to administration to the recipient bird, for example, by gene disruption and/or to introduce one or more heterologous nucleotide sequence(s). Methods of transiently or stably introducing a heterologous sequence into avian cells are known in the art (see e.g., U.S. Pat. No. 5,162,215 to Bosselman et al.). In one embodiment, the heterologous nucleotide sequence is stably incorporated into the PGC. Approaches for introducing nucleic acids of interest into recipient cells are known and include lipofection, transfection, microinjection, transformation, microprojectic techniques, etc. Any suitable vector can be used, including plasmids, viruses (including retroviruses), phage, and the like, whether in native form or derivatives thereof.

The donor PGCs can be genetically modified so as to produce a desired result in the recipient bird (e.g., to express a transgene that effects sex determination). Alternatively, it can be intended that the genetic modification be passed on to the offspring of the chimeric bird and produce a desired effect therein.

Introduction of one or more heterologous nucleotide sequence(s) (e.g., a foreign or exogenous sequence or an extra or modified copy of an endogenous sequence) can be used in a variety of applications, for example, to produce a polypeptide of interest in the bird (e.g., in the plasma or eggs of such birds for convenient collection and purification). According to this embodiment, the bird can be used essentially as a bioreactor. Polypeptides of interest include therapeutic (e.g., for veterinary or medical uses) or immunogenic (e.g., for vaccines) polypeptides, antibodies (including, but not limited to antibody fragments and single chain antibodies), enzymes (e.g., industrial enzymes), hormones and growth factors, or any other protein of interest.

Alternatively, the polypeptide can be a reporter polypeptide that serves as a marker of the donor cells (e.g., Green Fluorescent Protein, β-galactosidase, alkaline phosphatase, β-lactamase, neomycin phosphotransferase, and chloramphenicol acetyltransferase). Markers can be used to monitor embryonic development and/or analyze cell fate and migration, among other purposes (see e.g. Mozdziak et al. *Dev Dynamics* 226:439-445, 2003). This reference documents the first successful transgenic line of birds for cell fate analysis.

In other embodiments, the polypeptide is a therapeutic or immunogenic polypeptide or any other polypeptide that has a desired or beneficial effect on the recipient bird, e.g., a polypeptide that that has a desired phenotypic effect or enhances growth performance (including, but not limited to increased muscling and/or reduced fat deposition and/or improved feed to gain ratio), egg production, disease tolerance, and the like.

As a further alternative, the heterologous nucleic acid of interest can encode an antisense nucleic acid, a ribozyme (e.g., as described in U.S. Pat. No. 5,877,022) or any other non-translated RNA.

It will be understood by those skilled in the art that the heterologous nucleotide sequence(s) of interest can be operably linked to appropriate control sequences. For example, the heterologous nucleic acid can be operably linked to expression control elements including, but not limited to transcription/translation control signals, origins of replication, polyadenylation signals, and internal ribosome entry sites (IRES), promoters, enhancers, and the like.

It will further be appreciated that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign or exogenous, it is intended that the transcriptional initiation region is not found in the wild-type host into which the transcriptional initiation region is introduced. In particular embodiments, the heterologous nucleotide sequence(s) is operatively linked to the ovalbumin promoter or the lysozyme promoter.

In one embodiment, promoter/enhancer elements that are native to the target cell or subject to be treated are employed. In another embodiment, promoters/enhancer elements that are native to the heterologous nucleic acid sequence are employed. The promoter/enhancer element is chosen so that it will function in the target cell(s) of interest. In still another embodiment, avian promoter/enhancer elements are employed. The promoter/enhance element can be constitutive or inducible.

Inducible expression control elements can be employed in those applications in which it is desirable to provide regulation of the over expression of the heterologous nucleic acid sequence(s). Inducible promoters/enhancer elements for gene delivery can be cell- or tissue-specific promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metalothionein promoter.

In embodiments wherein which the heterologous nucleic acid sequence(s) will be transcribed and then translated in the target cells, specific initiation signals are generally required for efficient translation of inserted protein coding sequences. These exogenous translational control sequences, which can include the ATG initiation codon and adjacent sequences, can be of a variety of origins, both natural and synthetic.

V. Methods of Increasing the Proportion of Male Birds in a Plurality of Bird Eggs In birds, unlike mammals, it is the male that is the homogametic sex (ZZ) and the female which is the heterogametic sex (Zw). Therefore in birds, it is the female that determines the gender of the offspring since she produces ova that carry the sex determinative chromosome: i.e. either the Z or the w chromosome. Thus, as noted herein, by transferring male primordial germ cells to female embryonic hosts, the percentage of Z-bearing ova produced by that host is increased and the percentage of male offspring is increased. An increase in the percentage of male offspring from broiler flocks is economically desirable for the corresponding greater feed conversion ratio and more efficient meat production so obtained.

When the ZZ PGCs are administered to a male embryo, no sex ratio alteration should occur in the recipient's offspring regardless of the extent to which the donor PGCs colonize the recipient's gonad. It is only when ZZ PGCs are administered to female (Zw) recipient embryos that sex ratio skewing can occur. Thus, the instant method can produce sex ratio skewing when ZZ PGCs are administered to female (Zw) embryos.

The degree to which Z-bearing ova are produced in the recipient female embryo once it reaches sexual maturity, and thus the degree to which the recipient produces male offspring, can depend on the extent to which the donor ZZ PGCs colonize the gonad of the recipient embryo. Several possible outcomes can occur. At one end of the spectrum, the donor PGCs do not colonize the embryonic gonad, and thus the recipient would be expected to produce 50% Z ova and 50% w ova (i.e. no sex ratio skewing will occur). At the other end of the spectrum, the donor PGCs completely colonize the embryonic gonad to the exclusion of endogenous PGCs, the recipient would be expected to produce only Z ova, and thus all progeny of the recipient would be male. Accordingly, the expected percentage of male progeny that would be produced by a recipient female can be calculated as 50%+(the percent colonization of the embryonic gonad by ZZ PGCs divided by 2), assuming that the donor PGCs and the endogenous PGCs are individually equally capable of producing ova (i.e. the ova produced reflect the percentage of endogenous and donor PGCs present in the embryonic gonad).

Given this expectation, maximizing the percent colonization of the embryonic gonad by ZZ PGCs should maximize the percentage of male offspring of the recipient female. Several methods can be used to accomplish this goal. One such method is to administer a sufficient number of donor PGCs to the recipient such that the donor PGCs significantly outnumber endogenous PGCs. This approach would be expected to be most effective when the recipient embryo is at a stage prior to the stage at which PGCs migrate to the embryonic gonad.

Another method is to remove endogenous PGCs or inhibit their ability to colonize the embryonic gonad prior to the administration of donor PGCs. This can be accomplished by physically removing the endogenous PGCs from the embryo, for example, by removing the blood from the embryo at a stage when the endogenous PGCs are circulating in the embryonic blood. See Naito et al., *Mol Reprod Develop* 39:153, 1994; Tajima et al., *J Exp Zool* 280:265, 1998. However, this is a technically demanding manipulation that risks substantial damage to the embryo itself. An alternative is to prevent endogenous PGCs from reaching and/or colonizing the embryonic gonad. Several reports describe the use of chemicals or radiation to accomplish this goal, including busulfan (see Aige-Gil & Simkiss, *Res Vet Sci* 50:139, 1991; Vick et al., *J Reprod Fert* 98:637; Bresler et al., *Br Poutry Sci* 35:241, 1994; Hallett & Wentworth, *Poultr Sci* 70:1619, 1991), Concanavalin-A (Lee et al., *J Embryol Exp Morph* 46:5, 1978), and uv- or gamma-irradiation (Reynaud, *J Embryol Exp Morphol* 21:485-507, 1969; Reynaud, *J Roux's Arch Devel Biol* 179:85-110, 1976; Aige-Gil & Simkiss, *Br Poul Sci* 32:427-438, 1991; Reynaud, *C R Hebd Seances*

*Acad Sci-D: Sci Natur* 282:1195, 1976; Mraz & Woody, *Radiation Res* 54:63-68, 1973; Carsience et al., *Development* 117:669-75, 1993; Thoraval et al., *Poultry Sci* 73:1897-1905, 1994; Maeda et al., *Poultry Sci* 77:905-07, 1998). The use of toxic chemical and radiation is not optimal, however, especially for agriculturally important avian species.

An alternative approach is disclosed herein, in which antibodies that recognize antigens associated with PGCs are deposited into the yolk of the egg in which the recipient embryo develops as a result of immunization of the hen that produced the egg with the antigen. In this embodiment, female avians are immunized with an antigen associated with PGCs. Antibodies directed against the antigen are deposited into the yolk of eggs produced by the immunized females. The antibodies are then available to modulate the development of PGCs in an embryo growing within the egg. In one embodiment, the antibodies produce a reduction in the number of PGCs present in the embryonic gonad, such that when donor PGCs are administered into the recipient embryo, the donor PGCs are able to colonize the gonad and develop therein. The recipient embryo is then incubated to hatch, and allowed to reach sexual maturity.

When used for increasing the number or ratio of male birds hatched from a group of eggs, the presently disclosed subject matter involves administering to a female bird in ovo male (i.e. ZZ) avian primordial germ cells. The gender of the bird in ovo can be predetermined or determined after hatch. The bird is then incubated to hatch, the gender of the bird determined if necessary, raised to sexual maturity, and bred by crossing the bird with a suitable male breeder stock in accordance with known techniques. A plurality of fertile eggs laid by that bird are then collected, and typically incubated to hatch and the resulting birds grown for at least two to three weeks. The ratio of male to female bird eggs (or birds) produced from the female bird is greater than that obtained in the absence of administering the male primordial germ cells to that bird in ovo. Such methods are typically used on species of bird that are raised for meat production, such as chickens, turkeys, ducks, etc.

VI. Methods for Producing Avian Gametes

The presently disclosed subject matter also provides a method for producing avian gametes. In one embodiment, the method is employed to produce avian gametes from a second avian species in a first avian species. In one embodiment, the method comprises (a) immunizing a female of the first avian species with an antigen associated with primordial germ cells, whereby an egg produced by the female comprises a sufficiently high concentration of antibodies specific for the antigen to modulate PGC development of a recipient bird of the first avian species present within the egg; (b) introducing donor PGCs isolated from an avian of the second avian species into the recipient bird of the first avian species; (c) incubating the recipient bird of the first avian species to hatch; and (d) raising the recipient bird of the first avian species to sexual maturity, wherein the recipient bird of the first avian species produces gametes from the second avian species.

When used for the production and collection of avian gametes (sperm, ova), the primordial germ cells that are administered in ovo to a recipient species can be different from the donor species from which the donor PGCs were obtained. The recipient is then incubated to hatch and raised to sexual maturity, and sperm cells or ova of the donor species collected from the recipient animal, all in accordance with standard techniques. For example, in the case of an endangered species, the donor avian species can be a whooping crane, and the recipient avian species can be a sand hill crane. In another example concerning commercial poultry production, the donor avian species can be a turkey, and the recipient avian species can be a chicken.

U.S. Patent Application Publication No. 20030111016 describes approaches by the instant co-inventors to repopulate the embryonic gonad of one avian species with donor PGCs from another avian species. Barred Plymouth Rock (BPR) chicken embryos were incubated until stage 27-28 (H&H). Barred Plymouth Rock donor embryos were utilized as a color marker because they are homozygous recessive (ii) at the I locus and express pigment in their plumage. The gonads from male embryos were collected in DMEM, supplemented with 10% FBS, glutamine, antibiotic and antimycotic solution. Sex determination of the embryos was accomplished by utilizing the method of Petitte & Kegelmeyer (*Animal Biotechnol* 6:19-30, 1995). The gonads were then rinsed twice in PBS and incubated in 0.02% EDTA at 37 C for 15 minutes. Fresh media was added and the gonads were teased apart.

The cell suspension was collected and spun at 450 g for 5 minutes. The media was replaced and cell viability determined using trypan blue exclusion. Aliquots of the cell suspension were taken and stained with SSEA-1 antibody to determine the number of PGCs injected. Approximately 2-3 µl of cell suspension, containing 100-500 PGCs, was injected into the blood vessels of White Leghorn (WL) embryos at stages 14-17 (H&H) of development. The WL embryos served as recipients because they were known to be homozygous dominant (II). This genotype codes for an absence of pigment in the plumage. Following the PGC injection, the eggs were returned to the incubator to complete development. At hatching the phenotypic WL chicks were banded and subsequently grown to sexual maturity. The following test matings were conducted to determine if germline chimeras existed: male BPR×female WL and male WL×female BPR. The offspring from these test matings were subsequently evaluated to determine if male BPR gonadal PGC were incorporated in the WL. Since only male BPR embryos were used as donors, all "black" chicks (BPR-phenotype) derived from the male BPR×female WL test matings would be male.

Fertilized turkey eggs were incubated at 38.5° C. for 8-8.5 days (stage 27-28, H&H). Embryos were dissected to obtain gonads. Then 2-3 µl of the gonadal cell suspension, containing approximately 150 PGCs, was injected into the blood vessels stage 14 (H&H) chick embryos. The recipient eggs were sealed and returned to the incubator. Recipient embryos were collected at different stages of incubation (stage 19 to stage 25). The embryos were rinsed in PBS thrice and then fixed in 4% paraformaldehyde overnight at 4° C. Samples were washed three times in PBS and then placed in 50% ethanol. The tissues were then dehydrated, embedded in paraffin, and sectioned. The resulting sections were subsequently analyzed immunohistochemically by staining for SSEA-1 and periodic acid-Schiff (PAS). Previous research has identified a species difference in the expression of SSEA-1 by turkey and chick PGCs. This antigenic variation coupled with the standard PAS test can be used for identifying turkey-chick germline chimeras. Observations of the double stained chick embryonic sections verified that chick PGCs are both PAS positive and SSEA-1 positive. Double staining of the stage 24 turkey sections with PAS and SSEA-1 verified that turkey PGCs migrating through the dorsal mesentery and colonizing the gonad are PAS positive and do not express the SSEA-1 epitope. Hence, double staining of chick and turkey embryos verified that the double staining technique could be used as a marker for distinguishing PGCs from turkey versus PGCs from chicken.

Offspring from a WL (II)×BPR (ii) cross would typically express the WL phenotype (Ii) and exhibit an absence of melanin pigment in the plumage. The introduction of male BPR PGC into WL recipients resulted in offspring that demonstrated the black pigment pattern of the BPR. These data support the concept that there are no biological barriers that would prevent the production of increased male offspring by injecting female chick embryos with PGC isolated from the gonads of male embryos. However, the incidence of germline transmission was less than 1%. The low incidence of donor-derived offspring in this system was possibly related to the significant numerical advantage that endogenous PGCs exhibited when compared to the number of injected donor PGCs. The treatment of embryos with a BU+DMF+SO emulsion prior to the injection of donor PGC reduced the number of endogenous PGC by as much as 97%. When compared to BU+SO alone, the addition of DMF increased the reduction in endogenous PGC by approximately 15%.

Following the double staining with SSEA-1 and PAS; chick and turkey PGC were identified in the chick embryonic gonad on the basis of differing staining patterns. Due to the presence of glycogen, both chick and turkey PGCs stain a magenta color following PAS staining. However, turkey PGCs are no longer SSEA-1 positive when they take residence in the developing gonad, distinguishing them from PGCs of the chick which are SSEA-1 positive at this stage of development. These results suggest that PGCs isolated from the embryonic turkey gonad can be used to repopulate the chick gonad.

Continuing with reference to U.S. Patent Application Publication No. 20030111016, white leghorn (WL) embryos were treated in ovo with a busulfan emulsion (BU+DMF+ sesame oil) to deplete endogenous PGCs. Gonads from male Barred Plymouth Rock (BPR) embryos were collected, PGCs isolated, and the isolated PGCs administered to the busulfan emulsion treated birds and control untreated birds in ovo, essentially as described in the preceding example. After hatch, male WL chimeric birds were raised to sexual maturity and crossed with female BPR birds. Production of black offspring is indicative of transmission of the gametes derived from the BPR PGCs by the chimeric male WL parent. Results indicated that 25% (4/16) WL males are transmitting gametes derived from the BPR PGCs. Among these 4 chimeric birds, the rate of transmission is between about 2% to 23%. In the control birds that were not subjected to busulfan treatment, only one bird had any detectable transmission of the gametes derived from the BPR PGCs.

In some embodiments, the presently disclosed subject matter implements methods to repopulate the embryonic gonad of one avian species with donor PGCs from another avian species as disclosed in U.S. Patent Application Publication No. 20030111016. Of course, in such embodiments, the presently disclosed subject matter also implements the immunizing a female of the first avian species with an antigen associated with primordial germ cells, whereby an egg produced by the female comprises a sufficiently high concentration of antibodies specific for the antigen to modulate PGC development of a recipient bird of the first avian species present within the egg.

VII. Methods for Enhancing Germ Line Transmission of a Nucleic Acid Molecule

The presently disclosed subject matter also provides a method for enhancing germ line transmission of a nucleic acid molecule in a bird. In one embodiment, the method comprises (a) immunizing a female bird with an antigen associated with primordial germ cells, whereby an egg produced by the female bird comprises a sufficiently high concentration of antibodies specific for the antigen to modulate PGC development in a recipient bird present within the egg; (b) administering a plurality of donor PGCs comprising the nucleic acid molecule to the recipient bird under conditions sufficient to allow at least one of the plurality of PGCs to colonize a gonad of the recipient bird; (c) incubating the recipient bird to hatch; and (d) raising the recipient bird to sexual maturity, wherein the recipient bird produces gametes derived from the donor PGCs. In this embodiment, germ line transmission is rendered more efficient than current state of the art methods, in which the efficient generation of germ line chimeras continues to be a need in the art.

The instant method is based upon the same principles discussed hereinabove that relate to the production of germ line chimeras generally. In this embodiment, however, the donor PGCs are manipulated in vitro prior to administration into the recipient embryo by introducing into the PGCs an exogenous nucleic acid molecule (i.e. a transgene). The method is not limited either by the nucleic acid itself (for example, an open reading frame of interest operably linked to a promoter) or to the method of introduction (for example, electroporation, liposome-mediated transfection, etc.). Rather, a nucleic acid of interest is introduced into a plurality of donor PGCs using techniques known in the art, which are then administered to a recipient embryo developing in an egg produced by a female avian that had been immunized with an antigen associated with PGCs. The donor PGCs are then allowed to colonize the gonad of the embryo, which when it reaches sexual maturity, can transmit the nucleic acid to its offspring.

VIII. Administration

Primordial germ cells (PGCs) can be provided and formulated for carrying out the presently disclosed subject matter by any suitable technique, and stored, frozen, cultured, or the like prior to use as desired. For example, primordial germ cells can be collected from donor embryos at an appropriate embryonic stage. Stages of avian development are referred to herein by one of two art-recognized staging systems: the Eyal-Giladi & Kochav system (EG&K; see Eyal-Giladi & Kochav, *Dev Biol* 49:321-327, 1976), which uses Roman numerals to refer to pre-primitive streak stages of development, and the Hamburger & Hamilton staging system (H&H; see e.g., Hamburger & Hamilton, *J Morphol* 88:49-92, 1951), which uses Arabic numerals to reference to post-laying stages. Unless otherwise indicated, the stages referred to herein are stages as per the H&H staging system.

For example, PGCs can be isolated at stage 4, or the germinal crescent stage, through stage 30, with cells being collected from blood, genital ridge, or gonad in the later stages. The primordial germ cells are, in general, twice the size of somatic cells and easily distinguished and separated therefrom on the basis of size. Male (or homogametic) primordial germ cells (ZZ) can be distinguished from heterogametic primordial germ cells (Zw) by any suitable technique, such as collecting germ cells from a particular donor and typing other cells from that donor, the collected cells being of the same chromosome type as the typed cells.

PGCs can be formulated for administration to animals by dissociating the cells (e.g., by mechanical dissociation) and intimately admixing the cells with a pharmaceutically acceptable carrier (e.g., phosphate buffered saline solution). The primordial germ cells are in one embodiment gonadal primordial germ cells, and in another embodiment blood primordial germ cells ("gonad" or "blood" referring to their tissue of origin in the original embryonic donor). The primordial germ cells administered can be heterogametic (Zw) or homogametic (ZZ) depending upon the particular object of the administration. PGCs can be administered in physiologically acceptable carrier, in one embodiment at a pH of from about 6 to about 8 or 8.5, in a suitable amount to achieve the desired effect (e.g., 100 to 1000 PGCs per embryo). The PGCs can be administered free of other ingredients or cells, or other cells and ingredients can be administered along with the PGCs.

Administration of the primordial germ cells to the recipient animal in ovo can be carried out at any suitable time at which the PGCs can still migrate to the developing gonads. In one embodiment, administration is carried out from about stage IX according to the Eyal-Giladi & Kochav (EG&K) staging system to about stage 30 according to the Hamburger & Hamilton staging system of embryonic development, and in another embodiment, at stage 15. For chickens, the time of administration is thus during days 1, 2, 3, or 4 of embryonic development: in one embodiment day 2 to day 2.5. Administration is typically by injection into any suitable target site, such as the region defined by the amnion (including the embryo), the yolk sac, etc. In one embodiment, injection is into the embryo itself (including the embryo body wall), and in alternative embodiments, intravascular or intracoelomic injection into the embryo can be employed. The methods of the presently disclosed subject matter can be carried out with prior sterilization of the recipient bird in ovo (by "sterilization" is meant to render partially or completely incapable of producing gametes derived from endogenous PGCs). When donor gametes are collected from such a recipient, they can be collected as a mixture with gametes of the donor and the recipient. This mixture can be used directly, or the mixture can be further processed to enrich the proportion of donor gametes therein.

Administration of PGCs can be carried out by administering PGCs per se, or by administering precursor cells that develop into PGCs in the subject (particularly where the methods disclosed herein are employed to alter the sex ratio of offspring). For example, administration can be carried out by injecting the bird with blastodermal cells, where a subset of the blastodermal cells differentiates into primordial germ cells in vivo in the bird.

The in ovo administration of the primordial germ cells can be carried out by any suitable technique, either manually or in an automated manner. In one embodiment, in ovo administration is performed by injection. The mechanism of in ovo administration is not critical, but it is the mechanism should not unduly damage the tissues and organs of the embryo or the extraembryonic membranes surrounding it so that the treatment will not unduly decrease hatch rate. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole can be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria. It is envisioned that a high-speed injection system for avian embryos will be particularly suitable for practicing the presently disclosed subject matter. Numerous such devices are available, an exemplary device being the EMBREX INOVOJECT™ system (described in U.S. Pat. Nos. 4,681,063 and 4,903,625 to Hebrank), as well as devices described in U.S. Pat. Nos. 4,040,388; 4,469,047; and 4,593,646 to Miller. The disclosure of all United States patent references cited herein are be incorporated herein by reference in their entirety. All such devices, as adapted for practicing the methods disclosed herein, comprise an injector containing the a formulation of the primordial germ cells as described herein, with the injector positioned to inject an egg carried by the apparatus in the appropriate location within the egg as discussed above. In addition, a sealing apparatus operatively connected to the injection apparatus can be provided for sealing the hole in the egg after injection thereof.

EXAMPLES

The presently disclosed subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Example 1

Immunization of Female Birds

Antigenic peptide regions of chicken DAZL and chicken VASA homolog proteins were identified, synthesized, and conjugated to keyhole limpet hemocyanin (KLH). Selected peptides are shown in Table 1.

TABLE 1

Selected Peptides for Conjugation and Immunization of Laying Hens Against Chicken VASA and DAZL

| Designation | Amino Acid Sequences | Location of Peptide |
| --- | --- | --- |
| VASA-N | SRPSSPLSGFPGRPNS (SEQ ID NO: 3) | amino acids 42-57 of the chicken VASA homologue (CVH; GENBANK ® Accession No. BAB12337) |
| VASA-C | NPREMRMSYSETTFKS (SEQ ID NO: 4) | amino acids 645-660 of the chicken VASA homologue (CVH; GENBANK ® Accession No. BAB12337) |
| DAZL-N | SANAEAQCGSISEDNTH (SEQ ID NO: 7) | amino acids 2-18 of the chicken DAZL polypeptide (GENBANK ® Accession No. AAO26019) |
| DAZL-C | SQEDYFRERAHHFRKG (SEQ ID NO: 8) | amino acids 266-281 of the chicken DAZL polypeptide (GENBANK ® Accession No. AAO26019) |

Stock solutions (1,000 μg/ml) of the various conjugated peptides were maintained at 4° C. Immediately prior to immunization, a stable emulsion was produced from 0.5 ml of conjugated peptide and 0.5 ml of TITERMAX® adjuvant (TMA; CytRx Corp., Norcross, Ga., United States of America) utilizing two syringes connected by a double hub emulsifying needle. TMA is a synthetic nonionic block copolymer of polyoxyethylene and polyoxypropylene.

Sexually mature Leghorn females were immunized intramuscularly with 100-200 μg of a single conjugated peptide or combination of peptides (pectoralis major). Blood samples were taken after immunization, allowed to clot over night at 4° C., and the resulting serum samples were stored at −20° C. for subsequent antibody determination. A secondary immunization (50-100 μg of conjugated peptide+TMA) was administered 14 days later. Blood samples were also obtained three days following the second challenge from both immunized hens and non-injected controls. The resulting serum samples were stored at −20° C. for subsequent antibody determination.

Titers of anti-peptide antibodies were determined using an indirect ELISA technique. Antigen (i.e. KLH-conjugated peptide) solutions were prepared by dissolving the antigen in distilled water at a concentration of 20 μg/ml (1 mg in 50 ml). If the antigen was not immediately soluble, the pH was adjusted with 1N NaOH or 1N HCl until the antigen dissolved. To prepare ELISA plates, antigen solution (0.1 ml) was added to each well of a 96-well high-binding microtiter plate. The plate was then covered with an adhesive film and incubated overnight at room temperature or two hours at 37° C. Following the incubation period, the plates were washed three times with 200 μl of 0.05% Tween-20/PBS (pH 7.4, vol:vol). Plates were then blotted on paper towel to remove the excess Tween-20/PBS. Blocking solution (1% BSA in PBS, pH 7.4, stored at 4° C.) was then added (150 μl) to each well. Plates were covered with adhesive film and incubate at least 2 hr at room temperature or 1 hour at 37° C. or indefinitely at 4-8° C.

The plates were then washed an additional three times with 200 μl of 0.05% Tween-20/PBS (pH 7.4, vol:vol) and blotted on paper towel to remove the excess washing solution. Test or naive animal serum in 1% BSA/PBS buffer was serially diluted (1:100-1:1,000,000). Duplicate samples of 100 μl of the test or control (i.e. non-immunized) chicken serum dilutions were added. The plates were covered and incubated overnight at 4-8° C. or 2 hour at 37° C.

Plates were washed three times with 200 μl of 0.05% Tween-20/PBS (pH 7.4, vol:vol) and blotted on paper towel to remove the excess washing solution. 100 μl of goat or donkey anti-chicken (IgM+IgG) HRP conjugate solution (diluted 1:6000) in 1% BSA/PBS buffer was added to each well. The plates were covered with adhesive film and incubated at least 4 hour at room temperature or 2 hour at 37° C. or overnight at 4-8° C. Following incubation, the plates were once again washed three times with 200 μl of 0.05% Tween-20/PBS (pH 7.4, vol:vol) and blotted on paper towel to remove the excess washing solution.

Finally, 100 μl of substrate solution was added to each well. The substrate solution was prepared by adding 200 μl of a 2,2'-azino-bis-(3-benzthiazoline-6-sulfonic acid (ABTS) dye solution (prepared by dissolving 15 mg ABTS dye in 1 ml de-ionized water) and 10 μl $H_2O_2$ to 10 ml 0.05 M citrate buffer, pH 4.0. After addition of the substrate, the plates were allowed to incubate at room temperature and then analyzed on a plate reader at 405 nm. Titers were assigned as the last dilution that resulted in a signal that was statistically significantly higher than background (i.e. serum isolated from a non-immunized control hen) at 405 nm. Titers of antibodies from representative hens are shown in Table 2.

TABLE 2

Serum Titers Against Chicken VASA and DAZL Peptide Conjugates After Immunization of Laying Hens

| Bird # | Antigen | Titer 17 days after immunization | Titer 40 days after immunization |
|---|---|---|---|
| 522 | Vasa-C | 1:10,000 | 1:10,000 |
| 524 | Vasa-C | 1:1,000 | 1:5,000 |
| 538 | Dazl-C | 1:1,000 | 1:5,000 |
| 548 | Vasa-C | 1:1,000 | 1:5,000 |
|  | Vasa-N | 1:1,000 | 1:10,000 |
| 550 | Vasa-C | 1:1,000 | 1:5,000 |
|  | Vasa-N | 1:1,000 | 1:5,000 |
| 552 | Vasa-C | 1:500 | 1:1,000 |
|  | Vasa-N | 1:1,000 | 1:1,000 |
| 554 | Dazl-C | 1:10,000 | 1:50,000 |
|  | Dazl-N | 1:10,000 | 1:50,00 |

TABLE 2-continued

Serum Titers Against Chicken VASA and DAZL Peptide Conjugates After Immunization of Laying Hens

| Bird # | Antigen | Titer 17 days after immunization | Titer 40 days after immunization |
|---|---|---|---|
| 556 | Dazl-C | 1:100,000 | 1:100,000 |
|  | Dazl-N | 1:1,000,000 | 1:1,000,000 |
| 566 | Vasa-C | no reaction | 1:10,000 |
|  | Vasa-N | 1:10,000 | 1:50,000 |
|  | Dazl-C | no reaction | 1:5,000 |
|  | Dazl-N | 1:5,000 | 1:10,000 |

Example 2

Evaluation of PGCs in Stage 27 Embryos

After immunization, eggs were collected, stored for a maximum of 14 days, and incubated to reach stage 27 (H&H). Stage 27 (H&H) embryos were sacrificed and fixed in 4% paraformaldehyde overnight at 4° C. The embryos were then embedded in paraffin and serially sectioned across the gonadal region at 7 μm thickness. The slides containing gonadal region were selected from other slides and the PGCs in gonads were identified by immunohistogical staining using monoclonal antibody MC-480 (Developmental Studies Hybridoma Bank, The University of Iowa, Iowa City, Iowa, United States of America) that recognizes the stage-specific embyonic antigen-1 (SSEA-1). The immunohistogical staining was carried out using avidin-biotin conjugated alkaline phosphatase (VECTASTAIN® ABC-AP kit, Vector Laboratories, Burlingame, Calif., United States of America) and BCIP/NBT (5-bromo4-chloro-3-indolyl phosphate/nitroblue tetrazolium) substrate (Amresco, Inc., Solon, Ohio, United States of America). Briefly, after blocking in 1.5% normal goat serum in PBS for 30 minutes to eliminate nonspecific staining, sections were sequentially incubated at room temperature with the primary antibody (1:1000 diluted ascites) for 60 minutes and rinsed 3 times with PBS, biotinylated second antibody for 30 minutes rinsed 3 times with PBS, and ABC reagent for 30 minutes. After a final wash in PBS, sections were stained in the alkaline phosphatase substrate (NBT/BCIP solution, Amresco) for 15 minutes, and then mounted in an aqueous mounting medium. Representative sections are shown in FIGS. 1-3.

In FIG. 1, the hen that produced the egg in which the depicted embryo developed was immunized with peptides derived from the chicken VASA polypeptide. Panel A: control (no immunization); Panel B: immunization with Vasa-C peptide (SEQ ID NO: 4); Panel C: immunization with Vasa-N peptide (SEQ ID NO: 3); Panel D: immunization with both Vasa-N and Vasa-C. SSEA-1+ cells (dark stained cells) are much more abundant in the control embryo than in any of the embryos exposed to anti-VASA antibodies.

Figure 2:
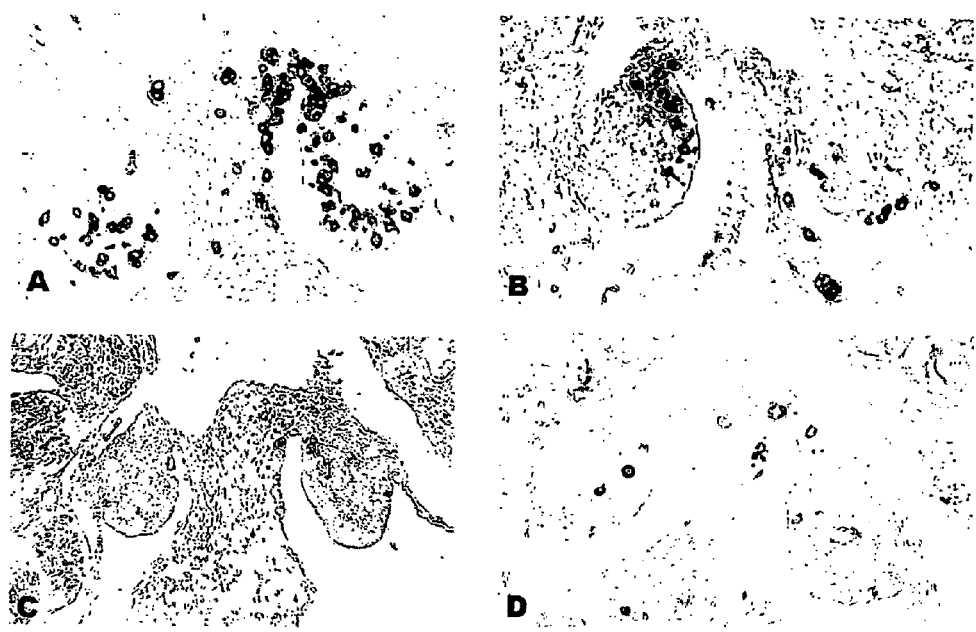

In FIG. 2, the hen that produced the egg in which the depicted embryo developed was immunized with peptides derived from the chicken DAZL polypeptide. Panel A: control (no immunization); Panel B: immunization with DAZL-C peptide (SEQ ID NO: 8); Panel C: immunization with DAZL-N peptide (SEQ ID NO: 7); Panel D: immunization with both DAZL-N and DAZL-C. SSEA-1+ cells (dark stained cells) are much more abundant in the control embryo than in any of the embryos exposed to anti-DAZL antibodies.

Figure 3:
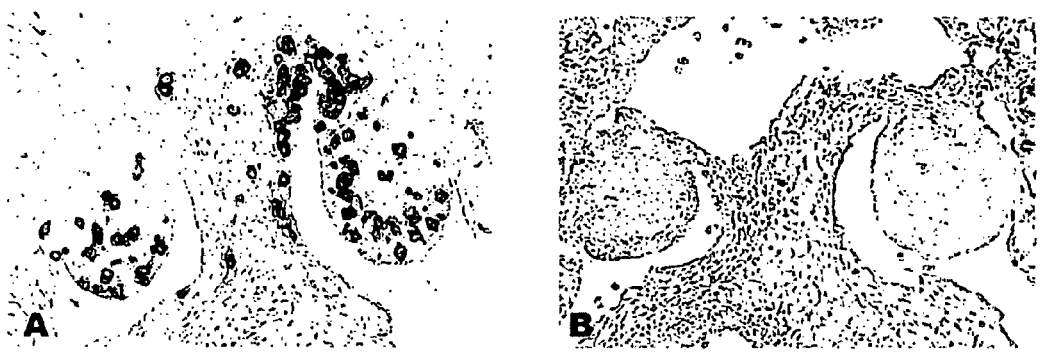

In FIG. 3, the hen that produced the egg in which the depicted embryo developed was immunized with peptides derived from both the chicken VASA and DAZL polypeptides. Panel A: control (no immunization); Panel B: immunization with Vasa-N, Vasa-C, DAZL-N, and DAZL-C peptides (SEQ ID NOs: 3, 4, 7, and 8). SSEA-1$^+$ cells (dark stained cells) are much more abundant in the control embryo than in the embryo exposed to both anti-VASA and anti-DAZL antibodies.

Figure 4:
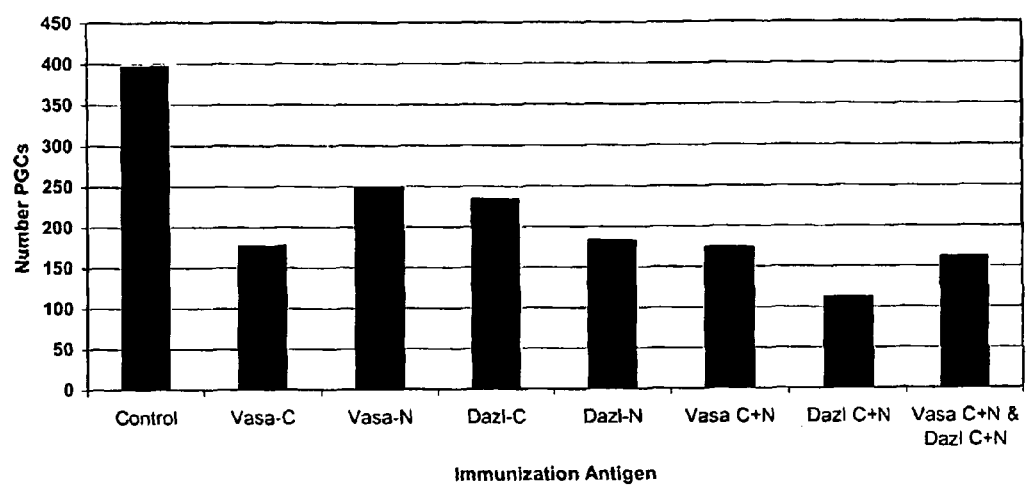
FIG. 4 is a bar graph that summarizes the results of examination of the sections described in FIGS. 1-3. Hens were immunized with the respective peptides and eggs were collected and incubated to reach embryonic stage 27. Embryos were processed for routine histology, serially sectioned, and immunostained with monoclonal antibody MC-480 (anti-SSEA-1) to identify germ cells in the developing gonads. The data presented represent the average number of PGCs counted in 10 sections from the gonadal ridge of embryos in eggs from 3 immunized hens for each peptide or combination of peptides.

Reduction of PGCs was determined by counting immunohistochemically stained PGCs in 10 sections of both left and right gonads of each embryo. The 10 sections were selected from the mid-region of the gonads. At least three sections were skipped between any two selected sections to avoid counting individual PGCs more than once. The results of this analysis are presented in FIG. 4. As shown in FIG. 4, each of the peptide antigens Vasa-N, Vasa-C, Dazl-N, and Dazl-C were able to induce an immune response in chickens, which resulted in the deposition of anti-antigen antibodies in the yolk of eggs produced by the immunized females. The presence of the antibodies in the eggs reduced PGCs numbers in developing stage 27 embryos. Immunizing females with individual peptides resulted in an approximately 35-55% reduction in endogenous PGC numbers, while immunization with two or more peptides simultaneously resulted in an approximately 55-70% reduction in endogenous PGCs.

Statistical analysis. Treatment differences for the average number of PGCs/embryo were analyzed using the GLM procedure of the SAS System (SAS Institute Inc., Cary, N.C., United States of America). The model was PGC=treatment hen. Treatment differences were significant at $p<0.0002$. Means were separated using Duncan's Multiple Range Test. All treatments were significantly different from Control with the exception of Vasa-N.

Example 3

Repopulating Germ Cells in Treated Embryos

Birds produced in accordance with Examples 1 and 2 are used as recipients and administered exogenous PGCs from donor birds.

A. Preparation of Donor Cells:

Gonads from 5.5-day chicken embryos are collected in PBS. The isolated gonads are pooled in 250 µl of 0.02% EDTA in a 35 mm petri dish and are incubated at 37° C. for 10 minutes. The gonads are teased with a needle in the petri dish and are incubated at 37° C. for 5 more minutes. The cells are collected in DMEM containing 20% FBS and centrifuged at 450 g for 5 minutes. The cells are washed and resuspended in DMEM. The cells number and viability are determined. The final concentration of viable cells is adjusted to about 1000 cells/µl.

B. Preparation of Recipient Embryos:

Recipient chick embryos are prepared as described in Examples 1 and 2. The embryos are placed in the incubator until Stage 14-17 (H&H).

C. Injection of Donor PGCs into Recipient Embryos:

Approximately 2 to 3 µl of gonadal cell suspension containing approximately 100 PGCs is injected into the blood vessel of stage 14-17 (H&H) recipient chick embryos. The recipient eggs are sealed and incubated at 37.5° C., 60% relative humidity.

D. Assessment of PGC Repopulation:

The embryos are collected at stage 27 (H&H) and fixed in 4% paraformaldehyde overnight at 4° C. The embryos are embedded in paraffin, sectioned at 7 µm thickness and stained immunohistochemically with SSEA-1 antibody. The number of PGCs in the left and right gonad in 10 randomly selected sections from control and PGC injected embryos is counted. The results are analyzed statistically by applying a t-test performed to test the null hypothesis that the difference between the means of the populations from which the two samples come equals 0.0 versus the alternative hypothesis that the difference is not equal to 0.0. If the p-value for this test is less than 0.05, the null hypothesis can be rejected at the 95.0% confidence level. Also determined is a 95.0% confidence interval for the difference between the population means. In repeated sampling, 95.0% of all such intervals will contain the true difference.

Example 4

Production of Intra-Specific Chicken Germline Chimeras after Depletion of Endogenous PGCs The following procedure is used to produce intra-specific germline chimeras:

A. Production of Intra-Specific Chicken Germline Chimeras

Barred Plymouth Rock (BPR) chicken embryos are incubated until stage 27-28 (H&H). Barred Plymouth Rock donor embryos are utilized as a color marker because they are homozygous recessive (ii) at the I locus and express pigment in their plumage. The gonads from male embryos are collected in DMEM, supplemented with 10% FBS, glutamine, antibiotic and antimycotic solution. Sex determination of the embryos is accomplished by utilizing the method of Petitte & Kegelmeyer (*Animal Biotechnol* 6:19-30, 1995). The gonads are then rinsed twice in PBS and incubated in 0.02% EDTA at 37° C. for 15 minutes. Fresh media is added and the gonads are teased apart.

The cell suspension is collected and spun at 450×g for 5 minutes. The media is replaced and cell viability determined using trypan blue exclusion. Aliquots of the cell suspension are taken and stained with SSEA-1 antibody to determine the number of PGCs injected. Approximately 2-3 µl of cell suspension, containing 100-500 PGCs, was injected into the blood vessels of White Leghorn (WL) embryos at stages 14-17 (H&H) of development. The WL embryos served as recipients because they were known to be homozygous dominant (II). This genotype codes for an absence of pigment in the plumage. Following the PGC injection, the eggs were returned to the incubator to complete development. At hatching the phenotypic WL chicks were banded and subsequently grown to sexual maturity. The following test matings were conducted to determine if germline chimeras existed: male BPR×female WL (BPR PGC) and male WL (BPR PGC)× female BPR. The offspring from these test matings were subsequently evaluated to determine if male BPR gonadal PGC were incorporated in the WL. Since only male BPR embryos were used as donors, all "black" chicks (BPR-phenotype) derived from the male BPR×female WL (BPR PGC) test matings would be male.

B. Preparation of Recipient Embryos:

Recipient chick embryos are prepared as described in Examples 1 and 2. The embryos are collected at stage 27 (H&H) and fixed in 4% paraformaldehyde overnight at 4° C. The embryos are embedded in paraffin, sectioned at 7 µm thickness and are stained immunohistochemically with SSEA-1 antibody. The number of PGCs in the left and right gonad in 10 randomly selected sections from each embryo is counted. The index of sterility (IS) is calculated using the equation $IS=(N-X)/N$ where N is the PGC number from control gonads and X is the PGC number from treated embryo (Reynaud, *J Embryol Exp Morphol* 21:485-507, 1969).

C. Production of Inter-specific Turkey-Chicken Embryonic Germline Chimeras

Fertilized turkey eggs are incubated at 38.5° C. for 8-8.5 days (stage 27-28, H&H). Embryos are dissected to obtain gonads. Then 2-3 µl of the gonadal cell suspension, containing approximately 150 PGCs, is injected into the blood vessels stage 14 (H&H) chick embryos. The recipient eggs are sealed and returned to the incubator. Recipient embryos are collected at different stages of incubation (stage 19 to stage 25). The embryos are rinsed in PBS thrice and then fixed in 4% paraformaldehyde overnight at 4° C. Samples are washed three times in PBS and then placed in 50% ethanol. The tissues are then dehydrated, embedded in paraffin, and sectioned. The resulting sections are subsequently analyzed immunohistochemically by staining for SSEA-1 and periodic acid-Schiff (PAS).

D. Results

Following the double staining with SSEA-1 and PAS, chick and turkey PGC are identified in the chick embryonic gonad on the basis of differing staining patterns. Due to the presence of glycogen, both chick and turkey PGC stain a magenta color following PAS staining. However, turkey PGC are no longer SSEA-1 positive when they take residence in the developing gonad, distinguishing them from PGC of the chick which are SSEA-1 positive at this stage of development.

Offspring from a WL (II)×BPR (ii) cross would typically express the WL phenotype (Ii) and exhibit an absence of melanin pigment in the plumage.

Example 5

Production of Intra-Specific Chimeras and Test Mating

Using similar protocols to those described in the previous Examples, white leghorn (WL) embryos are treated to deplete endogenous PGCs. Gonads from male Barred Plymouth Rock (BPR) embryos are collected, PGCs are isolated, and the isolated PGCs are administered to the treated birds and control untreated birds in ovo, essentially as described in the preceding example. After hatch, male WL (BPR PGC) chimeric birds are raised to sexual maturity and crossed with female BPR birds. Production of black offspring is indicative of transmission of the gametes derived from the BPR PGCs by the chimeric male WL (BPR PGC) parent.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of decreasing primordial germ cell (PGC) numbers in an avian embryo, the method comprising: a) immunizing a female avian with an immunogenic epitope of a DAZL polypeptide; and b) obtaining an egg comprising an embryo from the female avian, wherein the embryo has a decreased number of primordial germ cells (PGCs) as a result of the immunizing.

2. The method of claim 1, wherein the female avian is selected from the group consisting of chicken, turkey, duck, quail, and sand hill crane.

3. The method of claim 2, wherein the female avian is a chicken.

4. The method of claim 1, wherein the immunizing is with an immunogenic epitope of DAZL polypeptide and an immunogenic epitope of VASA polypeptide.

5. The method of claim 1, wherein the female avian is immunized with more than one immunogenic epitope of a DAZL polypeptide.

6. A method of inhibiting primordial germ cell (PGC) development in an avian embryo, the method comprising: a) immunizing a female avian with an immunogenic epitope of a DAZL polypeptide; and b) obtaining an egg comprising an embryo from the female avian, wherein development of primordial germ cells (PGCs) in the embryo is inhibited as a result of the immunizing.

7. The method of claim 6, wherein the immunizing is with an immunogenic epitope of DAZL polypeptide and an immunogenic epitope of VASA polypeptide.

8. The method of claim 6, wherein the female avian is selected from the group consisting of chicken, turkey, duck, quail, and sand hill crane.

9. The method of claim 8, wherein the female avian is a chicken.

10. The method of claim 6, wherein the female avian is immunized with more than one immunogenic epitope of a DAZL polypeptide.

11. A method of reducing primordial germ cell (PGC) numbers, inhibiting PGC development, or both in an avian embryo, the method comprising: a) immunizing a female chicken or turkey with an immunogenic epitope of a DAZL polypeptide, an immunogenic epitope of a VASA polypeptide, or a combination thereof; and b) obtaining an egg comprising an embryo from the female chicken or turkey, wherein the embryo has a decreased number of primordial germ cells (PGCs) and/or the development of PGCs in the embryo is inhibited as a result of the immunizing.

12. The method of claim 11, wherein the immunogenic epitope of a DAZL polypeptide comprises the amino acid sequence of SEQ ID NO: 7 or SEQ ID NO: 8 and/or the immunogenic epitope of a VASA polypeptide comprises the amino acid sequence of SEQ ID NO: 3 or SEQ ID NO: 4.

13. The method of claim 11, wherein the immunizing is with an immunogenic epitope of a DAZL polypeptide and an immunogenic epitope of a VASA polypeptide.

14. The method of claim 11, further comprising incubating the embryo to hatch.

15. The method of claim 11, wherein the female chicken or turkey is immunized with at least two immunogenic epitopes of a DAZL polypeptide.

16. A method of decreasing primordial germ cell (PGC) numbers, the method comprising: a) immunizing a female avian with an immunogenic epitope of a DAZL polypeptide, an immunogenic epitope of a VASA polypeptide, or a combination thereof; and b) obtaining an egg comprising an embryo from the female avian, wherein the embryo has a decreased number of primordial germ cells (PGCs) as a result of the immunizing.

17. The method of claim 16, wherein the female avian is immunized with at least two immunogenic epitopes of a DAZL polypeptide, at least two immunogenic epitopes of a VASA polypeptide, or at least one immunogenic epitope of a DAZL polypeptide and at least one immunogenic epitope of a VASA polypeptide.

* * * * *

SEQUENCE LISTING

```
<160> NUMBER OF SEQ ID NOS: 9

<210> SEQ ID NO 1
<211> LENGTH: 1989
<212> TYPE: DNA
<213> ORGANISM: Gallus gallus
<220> FEATURE:
<221> NAME/KEY: CDS
<222> LOCATION: (1)..(1989)

<400> SEQUENCE: 1 atg gag gag gac tgg gac acg gag ctg gag cag gag gcg gca gcg gct     48
Met Glu Glu Asp Trp Asp Thr Glu Leu Glu Gln Glu Ala Ala Ala Ala
1               5                   10                  15 tcc cag ggg cgt tct gag gag cag gcg tgg atg gct aac tct ggc aga     96
Ser Gln Gly Arg Ser Glu Glu Gln Ala Trp Met Ala Asn Ser Gly Arg
            20                  25                  30 cca aac agc cca tcc ctc cgc ttc tcc agc aga cca agc agc ccc ttg    144
Pro Asn Ser Pro Ser Leu Arg Phe Ser Ser Arg Pro Ser Ser Pro Leu
        35                  40                  45 tct ggc ttc cca ggc aga cca aac agc ccc ttc ttt ggc ttt agt cag    192
Ser Gly Phe Pro Gly Arg Pro Asn Ser Pro Phe Phe Gly Phe Ser Gln
    50                  55                  60 aat aaa ggc tca ctt ggt gct aat gaa gga ctt aac aga agt ctg cct    240
Asn Lys Gly Ser Leu Gly Ala Asn Glu Gly Leu Asn Arg Ser Leu Pro
65                  70                  75                  80 gtg cag cat gac att gga gga tat tct ggg agc aga gag tct gtt gta    288
Val Gln His Asp Ile Gly Gly Tyr Ser Gly Ser Arg Glu Ser Val Val
                85                  90                  95 cgt caa aac aga gaa gat caa cca gtg act aga ttt ggt aga ggg agg    336
Arg Gln Asn Arg Glu Asp Gln Pro Val Thr Arg Phe Gly Arg Gly Arg
            100                 105                 110 agt tct gga agc aga gat ttt caa gag agg aac tct gca aat gat cct    384
Ser Ser Gly Ser Arg Asp Phe Gln Glu Arg Asn Ser Ala Asn Asp Pro
        115                 120                 125 ggt atg caa gat caa ggt ttt aga aga gtt cct ggc atc ttt ggg caa    432
Gly Met Gln Asp Gln Gly Phe Arg Arg Val Pro Gly Ile Phe Gly Gln
    130                 135                 140 agc aag tgt ttt aac agt gag gaa aga aat agt cct ctg cgt ggc agc    480
Ser Lys Cys Phe Asn Ser Glu Glu Arg Asn Ser Pro Leu Arg Gly Ser
```

```
                        145                 150                 155                 160
cct ttt gcc cca gga gga aga gga gca gtt gga ggt cct gca gga gtt      528
Pro Phe Ala Pro Gly Gly Arg Gly Ala Val Gly Gly Pro Ala Gly Val
                        165                 170                 175 ctc aaa gga cgc tct gaa gaa att gat tct gga aga ggt cca aag gtg      576
Leu Lys Gly Arg Ser Glu Glu Ile Asp Ser Gly Arg Gly Pro Lys Val
            180                 185                 190 act tat gtc ccc cct cct cca cct gaa gat gaa cag tcc atc ttt gca      624
Thr Tyr Val Pro Pro Pro Pro Pro Glu Asp Glu Gln Ser Ile Phe Ala
                195                 200                 205 tgt tat cag tca gga att aat ttt gac aag tat gat gaa tgt gct gtt      672
Cys Tyr Gln Ser Gly Ile Asn Phe Asp Lys Tyr Asp Glu Cys Ala Val
        210                 215                 220 gag atg tca gga ctt gac cct cca gca cca tta ctg gct ttt gaa gaa      720
Glu Met Ser Gly Leu Asp Pro Pro Ala Pro Leu Leu Ala Phe Glu Glu
225                 230                 235                 240 gct aac ttt gct cag act tta agg aag aat ata tct aaa act gga tat      768
Ala Asn Phe Ala Gln Thr Leu Arg Lys Asn Ile Ser Lys Thr Gly Tyr
                    245                 250                 255 tca aaa ctt act cca gtg cag aag cac agc att cct gtt ata caa gca      816
Ser Lys Leu Thr Pro Val Gln Lys His Ser Ile Pro Val Ile Gln Ala
            260                 265                 270 ggg cgg gat tta atg tca tgt gcc cag aca gga tca gga aaa aca gca      864
Gly Arg Asp Leu Met Ser Cys Ala Gln Thr Gly Ser Gly Lys Thr Ala
        275                 280                 285 gct ttt ctt cta cca att gtg gac cgg atg atg aaa gat ggt gta act      912
Ala Phe Leu Leu Pro Ile Val Asp Arg Met Met Lys Asp Gly Val Thr
    290                 295                 300 gca agc ttc cca aag cag caa gac cca caa tgc att att gtt gca cca      960
Ala Ser Phe Pro Lys Gln Gln Asp Pro Gln Cys Ile Ile Val Ala Pro
305                 310                 315                 320 act aga gaa ctg ata aat cag atc ttc tta gaa gca agg aag ttt gtg     1008
Thr Arg Glu Leu Ile Asn Gln Ile Phe Leu Glu Ala Arg Lys Phe Val
                    325                 330                 335 tat ggg act tgt ata agg cct gtt gtg atc tat gga ggt aca cag aca     1056
Tyr Gly Thr Cys Ile Arg Pro Val Val Ile Tyr Gly Gly Thr Gln Thr
            340                 345                 350 ggt cat tca atc cgt caa ata atg caa ggc tgt aat ata tta tgt gcc     1104
Gly His Ser Ile Arg Gln Ile Met Gln Gly Cys Asn Ile Leu Cys Ala
        355                 360                 365 act cct gga agg ctt ctt gac att att gaa aaa ggg aag atc agt ttg     1152
Thr Pro Gly Arg Leu Leu Asp Ile Ile Glu Lys Gly Lys Ile Ser Leu
    370                 375                 380 gtg gag gtg aaa tat ttg gta cta gat gaa gca gac cgc atg ctc gat     1200
Val Glu Val Lys Tyr Leu Val Leu Asp Glu Ala Asp Arg Met Leu Asp
385                 390                 395                 400 atg ggt ttt gga tta gat atg aag aag ctg att tct tat cca gaa atg     1248
Met Gly Phe Gly Leu Asp Met Lys Lys Leu Ile Ser Tyr Pro Glu Met
                    405                 410                 415 cca tct aaa gac aga cgt caa aca tta atg ttt agt gcc act ttt cct     1296
Pro Ser Lys Asp Arg Arg Gln Thr Leu Met Phe Ser Ala Thr Phe Pro
            420                 425                 430 gag gaa gtt caa agg ctg gct ggt gaa ttt ttg aaa acg gac tat ata     1344
Glu Glu Val Gln Arg Leu Ala Gly Glu Phe Leu Lys Thr Asp Tyr Ile
        435                 440                 445 ttt ctt gtt att gga aat acc tgt gga gcc tgc agt gat gtt cag caa     1392
Phe Leu Val Ile Gly Asn Thr Cys Gly Ala Cys Ser Asp Val Gln Gln
    450                 455                 460 aat att ctt cag gtt ccc cgg tta tcc aag agg gat aaa cta ata gaa     1440
Asn Ile Leu Gln Val Pro Arg Leu Ser Lys Arg Asp Lys Leu Ile Glu
```

```
                465                 470                 475                 480
att cta caa agc aca ggt ggt gaa cga acc atg gtg ttt gtg gac aca      1488
Ile Leu Gln Ser Thr Gly Gly Glu Arg Thr Met Val Phe Val Asp Thr
                    485                 490                 495 aag aaa aaa gca gat tac ctt gca gcc ttt ctt tgt caa gag aac cta      1536
Lys Lys Lys Ala Asp Tyr Leu Ala Ala Phe Leu Cys Gln Glu Asn Leu
                500                 505                 510 cca tcc acc agc att cat gga gat agg gaa cag aga gag aga gag ata      1584
Pro Ser Thr Ser Ile His Gly Asp Arg Glu Gln Arg Glu Arg Glu Ile
            515                 520                 525 gct ctt cgc gat ttc cgt tct gga aaa tgt caa att ctt gtg gca act      1632
Ala Leu Arg Asp Phe Arg Ser Gly Lys Cys Gln Ile Leu Val Ala Thr
        530                 535                 540 tcg gta gca tca aga ggc ctg gat att gaa aat gtt caa cat gtt att      1680
Ser Val Ala Ser Arg Gly Leu Asp Ile Glu Asn Val Gln His Val Ile
545                 550                 555                 560 aat ttt gat ctc cct aac acc att gaa gat tat gta cat cga att gga      1728
Asn Phe Asp Leu Pro Asn Thr Ile Glu Asp Tyr Val His Arg Ile Gly
                    565                 570                 575 cga act ggt cgt tgt gga aat act ggc aaa gca gtt tca ttc ttt gat      1776
Arg Thr Gly Arg Cys Gly Asn Thr Gly Lys Ala Val Ser Phe Phe Asp
                580                 585                 590 gat cag tca gat ggc cat ctt gta caa tca cta ctt aaa gtg ctt tcc      1824
Asp Gln Ser Asp Gly His Leu Val Gln Ser Leu Leu Lys Val Leu Ser
            595                 600                 605 aga acc cag cag gaa ttc cag ttt ggt gga aga atg gct gtc caa aga      1872
Arg Thr Gln Gln Glu Phe Gln Phe Gly Gly Arg Met Ala Val Gln Arg
        610                 615                 620 aca aat att gtt gct tca act tgg tgc cca aag gga tta atg cag gcc      1920
Thr Asn Ile Val Ala Ser Thr Trp Cys Pro Lys Gly Leu Met Gln Ala
625                 630                 635                 640 gtg gca gaa tgg aac cca aga gaa atg agg atg tca tat tct gaa aca      1968
Val Ala Glu Trp Asn Pro Arg Glu Met Arg Met Ser Tyr Ser Glu Thr
                    645                 650                 655 aca ttt aag tca tgg gag taa                                          1989
Thr Phe Lys Ser Trp Glu
                660
```

<210> SEQ ID NO 2
<211> LENGTH: 662
<212> TYPE: PRT
<213> ORGANISM: Gallus gallus

<400> SEQUENCE: 2

```
Met Glu Glu Asp Trp Asp Thr Glu Leu Glu Gln Glu Ala Ala Ala
1               5                   10                  15

Ser Gln Gly Arg Ser Glu Glu Gln Ala Trp Met Ala Asn Ser Gly Arg
                20                  25                  30

Pro Asn Ser Pro Ser Leu Arg Phe Ser Arg Pro Ser Ser Pro Leu
            35                  40                  45

Ser Gly Phe Pro Gly Arg Pro Asn Ser Pro Phe Phe Gly Phe Ser Gln
        50                  55                  60

Asn Lys Gly Ser Leu Gly Ala Asn Glu Gly Leu Asn Arg Ser Leu Pro
65                  70                  75                  80

Val Gln His Asp Ile Gly Gly Tyr Ser Gly Ser Arg Glu Ser Val Val
                    85                  90                  95

Arg Gln Asn Arg Glu Asp Gln Pro Val Thr Arg Phe Gly Arg Gly Arg
                100                 105                 110

Ser Ser Gly Ser Arg Asp Phe Gln Glu Arg Asn Ser Ala Asn Asp Pro
```

```
            115                 120                 125
Gly Met Gln Asp Gln Gly Phe Arg Arg Val Pro Gly Ile Phe Gly Gln
130                 135                 140
Ser Lys Cys Phe Asn Ser Glu Glu Arg Asn Ser Pro Leu Arg Gly Ser
145                 150                 155                 160
Pro Phe Ala Pro Gly Arg Gly Ala Val Gly Pro Ala Gly Val
                165                 170                 175
Leu Lys Gly Arg Ser Glu Glu Ile Asp Ser Gly Arg Gly Pro Lys Val
                180                 185                 190
Thr Tyr Val Pro Pro Pro Pro Glu Asp Glu Gln Ser Ile Phe Ala
            195                 200                 205
Cys Tyr Gln Ser Gly Ile Asn Phe Asp Lys Tyr Asp Glu Cys Ala Val
210                 215                 220
Glu Met Ser Gly Leu Asp Pro Pro Ala Pro Leu Ala Phe Glu Glu
225                 230                 235                 240
Ala Asn Phe Ala Gln Thr Leu Arg Lys Asn Ile Ser Lys Thr Gly Tyr
                245                 250                 255
Ser Lys Leu Thr Pro Val Gln Lys His Ser Ile Pro Val Ile Gln Ala
                260                 265                 270
Gly Arg Asp Leu Met Ser Cys Ala Gln Thr Gly Ser Gly Lys Thr Ala
            275                 280                 285
Ala Phe Leu Leu Pro Ile Val Asp Arg Met Met Lys Asp Gly Val Thr
            290                 295                 300
Ala Ser Phe Pro Lys Gln Gln Asp Pro Gln Cys Ile Ile Val Ala Pro
305                 310                 315                 320
Thr Arg Glu Leu Ile Asn Gln Ile Phe Leu Glu Ala Arg Lys Phe Val
                325                 330                 335
Tyr Gly Thr Cys Ile Arg Pro Val Val Ile Tyr Gly Gly Thr Gln Thr
                340                 345                 350
Gly His Ser Ile Arg Gln Ile Met Gln Gly Cys Asn Ile Leu Cys Ala
            355                 360                 365
Thr Pro Gly Arg Leu Leu Asp Ile Ile Glu Lys Gly Lys Ile Ser Leu
370                 375                 380
Val Glu Val Lys Tyr Leu Val Leu Asp Glu Ala Asp Arg Met Leu Asp
385                 390                 395                 400
Met Gly Phe Gly Leu Asp Met Lys Lys Leu Ile Ser Tyr Pro Glu Met
                405                 410                 415
Pro Ser Lys Asp Arg Arg Gln Thr Leu Met Phe Ser Ala Thr Phe Pro
                420                 425                 430
Glu Glu Val Gln Arg Leu Ala Gly Glu Phe Leu Lys Thr Asp Tyr Ile
            435                 440                 445
Phe Leu Val Ile Gly Asn Thr Cys Gly Ala Cys Ser Asp Val Gln Gln
            450                 455                 460
Asn Ile Leu Gln Val Pro Arg Leu Ser Lys Arg Asp Lys Leu Ile Glu
465                 470                 475                 480
Ile Leu Gln Ser Thr Gly Gly Glu Arg Thr Met Val Phe Val Asp Thr
                485                 490                 495
Lys Lys Lys Ala Asp Tyr Leu Ala Ala Phe Leu Cys Gln Glu Asn Leu
                500                 505                 510
Pro Ser Thr Ser Ile His Gly Asp Arg Glu Gln Arg Glu Arg Glu Ile
            515                 520                 525
Ala Leu Arg Asp Phe Arg Ser Gly Lys Cys Gln Ile Leu Val Ala Thr
530                 535                 540
```

```
Ser Val Ala Ser Arg Gly Leu Asp Ile Glu Asn Val Gln His Val Ile
545                 550                 555                 560

Asn Phe Asp Leu Pro Asn Thr Ile Glu Asp Tyr Val His Arg Ile Gly
            565                 570                 575

Arg Thr Gly Arg Cys Gly Asn Thr Gly Lys Ala Val Ser Phe Phe Asp
        580                 585                 590

Asp Gln Ser Asp Gly His Leu Val Gln Ser Leu Leu Lys Val Leu Ser
    595                 600                 605

Arg Thr Gln Gln Glu Phe Gln Phe Gly Gly Arg Met Ala Val Gln Arg
    610                 615                 620

Thr Asn Ile Val Ala Ser Thr Trp Cys Pro Lys Gly Leu Met Gln Ala
625                 630                 635                 640

Val Ala Glu Trp Asn Pro Arg Glu Met Arg Met Ser Tyr Ser Glu Thr
            645                 650                 655

Thr Phe Lys Ser Trp Glu
            660

<210> SEQ ID NO 3
<211> LENGTH: 16
<212> TYPE: PRT
<213> ORGANISM: Gallus gallus

<400> SEQUENCE: 3

Ser Arg Pro Ser Ser Pro Leu Ser Gly Phe Pro Gly Arg Pro Asn Ser
1               5                   10                  15

<210> SEQ ID NO 4
<211> LENGTH: 16
<212> TYPE: PRT
<213> ORGANISM: Gallus gallus

<400> SEQUENCE: 4

Asn Pro Arg Glu Met Arg Met Ser Tyr Ser Glu Thr Thr Phe Lys Ser
1               5                   10                  15

<210> SEQ ID NO 5
<211> LENGTH: 1882
<212> TYPE: DNA
<213> ORGANISM: Gallus gallus
<220> FEATURE:
<221> NAME/KEY: CDS
<222> LOCATION: (174)..(1043)

<400> SEQUENCE: 5
cctctttcac acccctctta aaaagaaaaa gaaagaaaaa aaagacaaaa aaaaatacaa      60
acacaaaaaa gtggggttct ttagtatctg tttttcccaac actcctattg ttttttgtctt  120 gaaggcctcg tttgttttta agtgtgcggg cgctgtcaca gctccgggga acg atg         176
                                                            Met
                                                            1 tct gca aat gcg gaa gcc cag tgt gga agt atc tca gag gat aat acc      224
Ser Ala Asn Ala Glu Ala Gln Cys Gly Ser Ile Ser Glu Asp Asn Thr
        5                   10                  15 cat tcg tca aca acc tgc caa gga tat gtt tta cca gaa gga aaa atc    272
His Ser Ser Thr Thr Cys Gln Gly Tyr Val Leu Pro Glu Gly Lys Ile
            20                  25                  30 atg cca aat aca gtc ttt gtt ggt gga att gat ata agg atg aat gaa    320
Met Pro Asn Thr Val Phe Val Gly Gly Ile Asp Ile Arg Met Asn Glu
        35                  40                  45 gca gaa att cgg agt tac ttt gaa caa tat ggt act gtg aag gag gtg    368
Ala Glu Ile Arg Ser Tyr Phe Glu Gln Tyr Gly Thr Val Lys Glu Val
50                  55                  60                  65
```

```
aaa ata atc act gac aga act ggt gtt tcc aaa ggg tat gga ttt gtt       416
Lys Ile Ile Thr Asp Arg Thr Gly Val Ser Lys Gly Tyr Gly Phe Val
                 70                  75                  80 tca ttc ctg gac aat gtg gat gtt caa aag ata gta gaa tca cag atc       464
Ser Phe Leu Asp Asn Val Asp Val Gln Lys Ile Val Glu Ser Gln Ile
             85                  90                  95 agt gtc cat gga aaa agg ctg aaa ctg gga cca gca att aga aaa caa       512
Ser Val His Gly Lys Arg Leu Lys Leu Gly Pro Ala Ile Arg Lys Gln
        100                 105                 110 caa aac ttg tgt tct tac atg cag cct aga cca ttg gct ttc aat cct       560
Gln Asn Leu Cys Ser Tyr Met Gln Pro Arg Pro Leu Ala Phe Asn Pro
    115                 120                 125 cct gca ccg caa ttc cat agc gta tgg act aat caa aat aca gag acc       608
Pro Ala Pro Gln Phe His Ser Val Trp Thr Asn Gln Asn Thr Glu Thr
130                 135                 140                 145 tac gtg cag cct caa gct gtg gtg agc cca cta act cag tat gtc cag       656
Tyr Val Gln Pro Gln Ala Val Val Ser Pro Leu Thr Gln Tyr Val Gln
                150                 155                 160 acg tat gcg tac agt tca cca gct gta ttg ata cag cag caa gtt cct       704
Thr Tyr Ala Tyr Ser Ser Pro Ala Val Leu Ile Gln Gln Gln Val Pro
             165                 170                 175 gta gga tat cag cca gca tac aac tat cag gct cca cca cag tgg gtt       752
Val Gly Tyr Gln Pro Ala Tyr Asn Tyr Gln Ala Pro Pro Gln Trp Val
        180                 185                 190 cct ggg gag caa aga aac tac gtt atg cct ccg gtt tat act tca gta       800
Pro Gly Glu Gln Arg Asn Tyr Val Met Pro Pro Val Tyr Thr Ser Val
    195                 200                 205 aac tat cac tac agt gag gat cca gaa ttt ata caa aca gaa tgt gct       848
Asn Tyr His Tyr Ser Glu Asp Pro Glu Phe Ile Gln Thr Glu Cys Ala
210                 215                 220                 225 gtc cca gag ccc aca cag atg tct ggt aat agt cca caa aaa aag tct       896
Val Pro Glu Pro Thr Gln Met Ser Gly Asn Ser Pro Gln Lys Lys Ser
                230                 235                 240 gtg gac agg agc ata caa aca gta gta tcc tgt ctg ttt aac cct gaa       944
Val Asp Arg Ser Ile Gln Thr Val Val Ser Cys Leu Phe Asn Pro Glu
             245                 250                 255 aac cgt ctg agg aac acc ttt gta tca caa gaa gac tac ttc agg gag       992
Asn Arg Leu Arg Asn Thr Phe Val Ser Gln Glu Asp Tyr Phe Arg Glu
        260                 265                 270 agg agg gcg cat cac ttc aga aaa gga aga gca gtg ctc aaa agt gtt      1040
Arg Arg Ala His His Phe Arg Lys Gly Arg Ala Val Leu Lys Ser Val
    275                 280                 285 tga tgaacaaaga ctttgaagta cataaatgta ttactttgat gttcctacag           1093
ttcagtttag taagatgtgt agtaaaaagt gtaaccttgt tcaaaaagtt gcttcaagtt    1153
gatgtttgtg ttctgtttta cctgttccag aatagctatt tttgcttgag aagtttgaag   1213
ttgtaagagt tgaaatattt ccaggtttta ttactagctt gcatgctttt cctgctaact   1273
aactgaaatg ctaatcttaa ggaatttata tggggaaggg gaaaaagaa aaacactttg    1333 tttggtatgt gtggattttc ttctgagctt taaggtacag tttgttgcat gttaaatttt   1393
agttcttatt aaaccacaac tttaagttac taacgtcaac cagttacctc ttgcagttca   1453
aaagttgaag cagttccttg tccaagatgg agtattttaa aactgagctc ttaatcagtg   1513
gaacagaaga cgtcacggtg taactcaact gaagcccttt aagtcccggt tctctttaga   1573
ctacctaatc aatgtctttg tttgctaacg acagttcatc tatgtgaatc taaaattcc    1633 tatatgtaac ttaagatgca agaatgtaat tagttacatt ggctgctcag tggagtatga   1693
cttttttttt tactggatta attttagcaa tacctgtatc ttaaaattgt gagaaaatac   1753
```

```
tgcatttaaa atatgcctaa ctttgtgacg caatatgtta atcaaagaat acatgtaagc    1813
atattttaaa aataattatg tagattttag tcatgtattt tgaaacaatt aaaatttta     1873 attttgact                                                            1882
```

<210> SEQ ID NO 6
<211> LENGTH: 289
<212> TYPE: PRT
<213> ORGANISM: Gallus gallus

<400> SEQUENCE: 6

```
Met Ser Ala Asn Ala Glu Ala Gln Cys Gly Ser Ile Ser Glu Asp Asn
1               5                   10                  15

Thr His Ser Ser Thr Thr Cys Gln Gly Tyr Val Leu Pro Glu Gly Lys
            20                  25                  30

Ile Met Pro Asn Thr Val Phe Val Gly Gly Ile Asp Ile Arg Met Asn
        35                  40                  45

Glu Ala Glu Ile Arg Ser Tyr Phe Glu Gln Tyr Gly Thr Val Lys Glu
    50                  55                  60

Val Lys Ile Ile Thr Asp Arg Thr Gly Val Ser Lys Gly Tyr Gly Phe
65                  70                  75                  80

Val Ser Phe Leu Asp Asn Val Asp Val Gln Lys Ile Val Glu Ser Gln
                85                  90                  95

Ile Ser Val His Gly Lys Arg Leu Lys Leu Gly Pro Ala Ile Arg Lys
            100                 105                 110

Gln Gln Asn Leu Cys Ser Tyr Met Gln Pro Arg Pro Leu Ala Phe Asn
        115                 120                 125

Pro Pro Ala Pro Gln Phe His Ser Val Trp Thr Asn Gln Asn Thr Glu
    130                 135                 140

Thr Tyr Val Gln Pro Gln Ala Val Val Ser Pro Leu Thr Gln Tyr Val
145                 150                 155                 160

Gln Thr Tyr Ala Tyr Ser Ser Pro Ala Val Leu Ile Gln Gln Gln Val
                165                 170                 175

Pro Val Gly Tyr Gln Pro Ala Tyr Asn Tyr Gln Ala Pro Pro Gln Trp
            180                 185                 190

Val Pro Gly Glu Gln Arg Asn Tyr Val Met Pro Pro Val Tyr Thr Ser
        195                 200                 205

Val Asn Tyr His Tyr Ser Glu Asp Pro Glu Phe Ile Gln Thr Glu Cys
    210                 215                 220

Ala Val Pro Glu Pro Thr Gln Met Ser Gly Asn Ser Pro Gln Lys Lys
225                 230                 235                 240

Ser Val Asp Arg Ser Ile Gln Thr Val Val Ser Cys Leu Phe Asn Pro
                245                 250                 255

Glu Asn Arg Leu Arg Asn Thr Phe Val Ser Gln Glu Asp Tyr Phe Arg
            260                 265                 270

Glu Arg Arg Ala His His Phe Arg Lys Gly Arg Ala Val Leu Lys Ser
        275                 280                 285

Val
```

<210> SEQ ID NO 7
<211> LENGTH: 17
<212> TYPE: PRT
<213> ORGANISM: Gallus gallus

<400> SEQUENCE: 7

```
Ser Ala Asn Ala Glu Ala Gln Cys Gly Ser Ile Ser Glu Asp Asn Thr
```

```
1               5                  10                 15
His

<210> SEQ ID NO 8
<211> LENGTH: 16
<212> TYPE: PRT
<213> ORGANISM: Gallus gallus

<400> SEQUENCE: 8

Ser Gln Glu Asp Tyr Phe Arg Glu Arg Ala His His Phe Arg Lys Gly
1               5                   10                  15

<210> SEQ ID NO 9
<211> LENGTH: 4
<212> TYPE: PRT
<213> ORGANISM: Gallus gallus

<400> SEQUENCE: 9

Asp Glu Ala Asp
1
```